(12) United States Patent
Booth

(10) Patent No.: US 8,680,152 B2
(45) Date of Patent: Mar. 25, 2014

(54) CATHEPSIN INHIBITORS FOR THE TREATMENT OF BONE CANCER AND BONE CANCER PAIN

(75) Inventor: Robert Booth, Los Altos Hills, CA (US)

(73) Assignee: Virobay, Inc., Menlo Park, CA (US)

( * ) Notice: Subject to any disclaimer, the term of this patent is extended or adjusted under 35 U.S.C. 154(b) by 0 days.

(21) Appl. No.: 13/462,587

(22) Filed: May 2, 2012

(65) Prior Publication Data

US 2012/0282267 A1    Nov. 8, 2012

Related U.S. Application Data

(60) Provisional application No. 61/481,628, filed on May 2, 2011.

(51) Int. Cl.

| | | |
|---|---|---|
| A61K 38/00 | (2006.01) | |
| A61P 19/08 | (2006.01) | |
| A01N 37/18 | (2006.01) | |
| A61K 31/16 | (2006.01) | |
| A61K 39/395 | (2006.01) | |

(52) U.S. Cl.
USPC .................. 514/616; 514/16.7; 424/146.1

(58) Field of Classification Search
None
See application file for complete search history.

(56) References Cited

U.S. PATENT DOCUMENTS

2009/0176861 A1 * 7/2009 Bayly et al. ................... 514/425

FOREIGN PATENT DOCUMENTS

| WO | WO 99/48911 A1 | 9/1999 |
|---|---|---|
| WO | WO 01/09169 A2 | 2/2001 |
| WO | WO 2006/102243 A2 | 9/2006 |
| WO | WO 2006102243 A2 * | 9/2006 |

OTHER PUBLICATIONS

Zhang D "Inhibition of Prostate Cancer Skeletal Metastases by Targeting Cathepsin K" http://www.dtic.mil/dtic/tr/fulltext/u2/a535353.pdf, published Feb. 2010.*

Elie et al "Identification and pre-clinical testing of a reversible cathepsin protease inhibitor reveals anti-tumor efficacy in a pancreatic cancer model" Biochimie 92:1618-1624, published May 4, 2010.*

Kim, W. et al., "Recent developments of cathepsin inhibitors and their selectivity," Expert Opinion on Therapeutic Patents 2002, vol. 12, No. 3, pp. 419-432.

Nomura, Toshiyuki et al., "Involvement of cathepsins in the invasion, metastasis and proliferation of cancer cells," The Journal of Medical Investigation, Feb. 2005, vol. 52, No. 1-2, pp. 1-9.

Katunuma, Nobuhiko, "Structure-based development of specific inhibitors for individual cathepsins and their medical applications," Proceedings of the Japan Academy Series B Physical and Biological Sciences, Feb. 2011, vol. 87, No. 2, pp. 29-39.

Elie, B. et al., "Identification and pre-clinical testing of a reversible cathepsin protease inhibitor reveals anti-tumor efficacy in a pancreatic cancer model," Biochimie, Masson, Paris, France, Nov. 1, 2010, vol. 92, No. 11, pp. 1618-1624.

* cited by examiner

*Primary Examiner* — Cecilia J Tsang
*Assistant Examiner* — Zachary J Miknis
(74) *Attorney, Agent, or Firm* — Kilpatrick Townsend & Stockton LLP

(57) ABSTRACT

The present invention is directed to methods of using compounds that are inhibitors of cysteine proteases, in particular, of both cathepsins S and K and optionally further cathepsins B and/or L in treating bone cancer. The present invention is directed to pharmaceutical compositions comprising these compounds for treating bone cancer and bone cancer pain, especially the pain associated with metastasis. A single compound can be used to ameliorate the pain, the injury to bone, while also reducing tumor growth, the risk of metastasis and/or invasiveness of the cancer.

8 Claims, 11 Drawing Sheets

FIGURE 1

| CatS | CatL | CatB | CatK | CatF | CatV |
|---|---|---|---|---|---|
| <250pM | <250pM | 330pM | 2.3nM | 4.7nM | <250pM |

No inhibition (IC$_{50}$>10μM) of a panel of cysteine, serine, and aspartyl proteases: caspase 3, chymotrypsin, cathepsin D, cathepsin H, cathepsin X/Z, neutrophil elastase, MMP9, thrombin

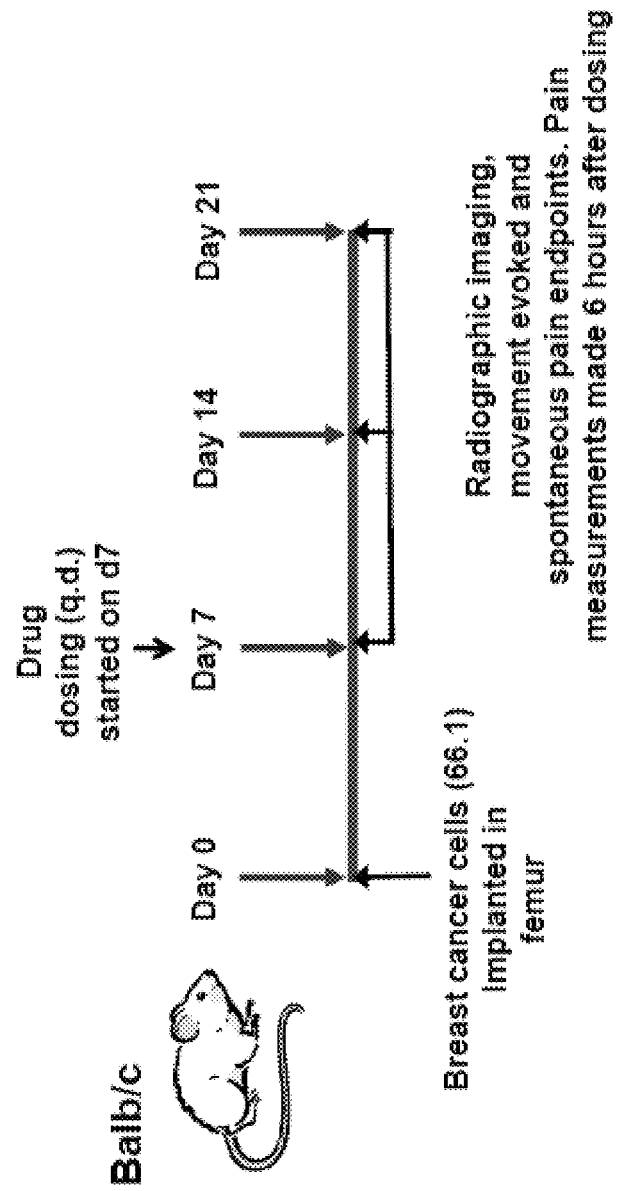

FIGURE 5

| Inhibitors | Enzyme IC$_{50}$ (nM) | | | | | |
|---|---|---|---|---|---|---|
| | CatS | CatL | CatB | Hu CatK | CatK (HuRab) | CatF | CatV |
| Cmpd A | 0.009 | <0.25 | 0.33 | ND | 2.3 | 4.7 | <0.25 |

| | Enzyme IC$_{50}$ (nM) | | | | | |
|---|---|---|---|---|---|---|
| | CatS | CatL | CatB | Hu CatK | CatK (HuRab) | CatF | CatV |
| Cmpd B | 0.46 | 0.29 | 3.2 | ND | 0.96 | 30 | <0.25 |
| Cmpd C | 0.006 | <0.25 | <0.25 | ND | 0.06 | <0.25 | <0.25 |

CATHEPSIN INHIBITORS FOR THE TREATMENT OF BONE CANCER AND BONE CANCER PAIN

CROSS-REFERENCES TO RELATED APPLICATIONS

This application claims the benefit of U.S. Provisional Patent Application No. 61/481,628, filed May 2, 2011, which is hereby incorporated by reference in its entirety for all purposes.

FIELD OF THE INVENTION

The present invention is directed to compounds and compositions that are inhibitors of cysteine cathepsin S and K and also to methods of treating bone cancer and, more particularly, bone cancer pain.

BACKGROUND OF THE INVENTION

Cysteine proteases represent a class of peptidases characterized by the presence of a cysteine residue in the catalytic site of the enzyme. Cysteine proteases are associated with the normal degradation and processing of proteins. The aberrant activity of cysteine proteases, e.g., as a result of increased expression or enhanced activation, however, may have pathological consequences. In this regard, certain cysteine proteases are associated with a number of disease states, including arthritis, muscular dystrophy, inflammation, tumor invasion, glomerulonephritis, malaria, periodontal disease, metachromatic leukodystrophy and others. For example, increased cathepsin B levels and redistribution of the enzyme are found in tumors; thus, suggesting a role for the enzyme in tumor invasion and metastasis. In addition, aberrant cathepsin B activity is implicated in such disease states as rheumatoid arthritis, osteoarthritis, pneumocystis carinii, acute pancreatitis, inflammatory airway disease and bone and joint disorders.

The prominent expression of cathepsin K in osteoclasts and osteoclast-related multinucleated cells and its high collagenolytic activity suggest that the enzyme is involved in osteoclast-mediated bone resorption and, hence, in bone abnormalities such as occurs in osteoporosis. In addition, cathepsin K expression in the lung and its elastinolytic activity suggest that the enzyme plays a role in pulmonary disorders as well.

Cathepsin L is implicated in normal lysosomal proteolysis as well as in several disease states, including, but not limited to, metastasis of melanomas. Cathepsin S is implicated in Alzheimer's disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis, neuropathic pain, and Hashimoto's thyroiditis. In addition, cathepsin S is implicated in: allergic disorders, including, but not limited to asthma; and allogeneic immune reponses, including, but not limited to, rejection of organ transplants or tissue grafts.

In view of the number of diseases wherein it is recognized that an increase in cysteine protease activity contributes to the pathology and/or symptomatology of the disease, molecules which inhibit the activity of more than one of this class of enzymes, in particular molecules which inhibit cathepsin S and at least one other cathepsin selected from B, K, and L will therefore be especially useful as therapeutic agents with respect to treating bone cancer and bone cancer pain.

BRIEF SUMMARY OF THE INVENTION

In its various aspects, the invention provides methods of treating a metastatic cancer in bone, said method comprising administration to a subject in need thereof a therapeutically effective amount of an inhibitor of cathepsin S and K ("a cathepsin S/K inhibitor"). In some embodiments, the inhibitor is a cathepsin S/K inhibitor and also an inhibitor of cathepsin L and/or B (a "cathepsin S/K/L inhibitor" or a "cathepsin S/K/B inhibitor," respectively), or an inhibitor of cathepsins S, K, L and B ("a cathepsin S/K/L/B inhibitor"). In some embodiments, the metastatic cancer is a multiple myeloma, a melanoma, a head and neck cancer, a breast cancer, a prostate cancer, a kidney cancer or a lung cancer. In some embodiments, the methods reduce metastasis to bone, reduce bone cancer pain, or reduce bone erosion, loss or damage (e.g., microfractures, bone distortion, disruption of bone periosteum), associated with the cancer or its metastasis to bone. In some embodiments accordingly the invention provides methods of treating metastatic cancer bone pain (e.g., inflammatory pain, neuropathic pain, allodynia, nerve pain, or breakthrough pain, cancer-induced hypersensitivity to pain). In some embodiments, the pain is due to bone microfactures, bone distortion, bone mechanical stress, or disruption of the periosteum with stretching and entrapment of nerves associated with the cancer. In some embodiments, the cancer is an osteolytic metastasis or an osteoblastic metastasis. In some embodiments, both a cancer pain and a bone disease associated with the cancer are treated by the single compound. In some embodiments, tumor angiogenesis and invasiveness are inhibited by the compound. In some embodiments, the compounds of the invention act directly on pain mechanisms, bone homeostasis mechanisms, and tumor invasiveness or angiogenesis to treat the bone cancer or bone cancer pain.

In any of the above embodiments, the cathepsin inhibitor for use according to the invention is a cathepsin S/K inhibitor, a cathepsin S/K/B inhibitor, a S/K/L inhibitor, or a cathepsin S/L/K/B inhibitor of Formula (I):

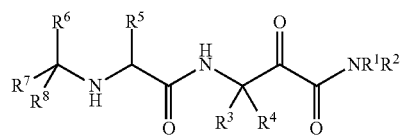

where: $R^1$ is hydrogen or alkyl; $R^2$ is cycloalkyl or cycloalkylalkyl optionally substituted with one or two substituents independently selected from alkyl, alkoxy, or halo; $R^3$ is hydrogen or alkyl; $R^4$ is hydrogen, alkyl, or cycloalkylalkyl; and $R^5$ is haloalkyl, (alkylene or haloalkylene)-X—$R^9$ (where X is a bond, —O—, —S—, —SO—, —SO$_2$—, or —NHSO$_2$—) and $R^9$ is alkyl, haloalkyl, cycloalkyl, cycloalkylalkyl, pyridinyl, pyridinylalkyl, phenylalkyl or phenyl) wherein the alicyclic, phenyl or pyridinyl ring in $R^5$ is optionally substituted with one, two, or three $R^a$ members independently selected from alkyl, haloalkyl, alkoxy, hydroxy, halo, and haloalkoxy or optionally substituted with one or two $R^b$ members independently selected from hydrogen, alkyl, haloalkyl, alkoxy, hydroxy, haloalkoxy, halo, and one $R^c$ member selected from —SO$_2$R$^{11}$ (where R$^{11}$ is alkyl); $R^6$ is hydrogen, or haloalkyl; $R^7$ is hydrogen, alkyl, or haloalkyl; and $R^8$ hydrogen, phenyl or phenoxy-CF$_2$— wherein the phenyl or phenoxy ring is-optionally substituted with one, two, or three $R^e$ members independently selected from alkyl, halo, haloalkyl, hydroxy, alkoxy, and haloalkoxy, or a pharmaceutically acceptable salt thereof. In preferred embodiments, each halo of the above formula is fluoro. In one embodiment, $R^6$ and $R^7$ are each hydrogen and $R^8$ is 4-fluorophenoxy-$CF_2$—. In yet other embodiments, the $R^5$ is haloalkyl. In still other embodiments, X is —$SO_2$—. When X is —$SO_2$—$R^9$ is preferably cycloalkyl, cycloalkylalkyl, phenyl, phenylalkyl, pyridinyl, or pyridinyl alkyl. More generally $R^9$ is also contemplated to be substituted or unsubstituted phenyl, phenylalkyl, pyridinyl, or pyridinylalkyl. In other embodiments, including any set forth above, $R^2$ is cycloalkyl and $R^1$ is hydrogen. In yet other embodiments of any of the above, $R^3$ is hydrogen and $R^4$ is alkyl. Particularly preferred inhibitors include the following three compounds and their pharmaceutically acceptable salts:

Compound A

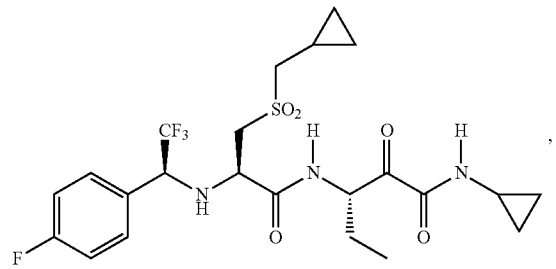

,

Compound B

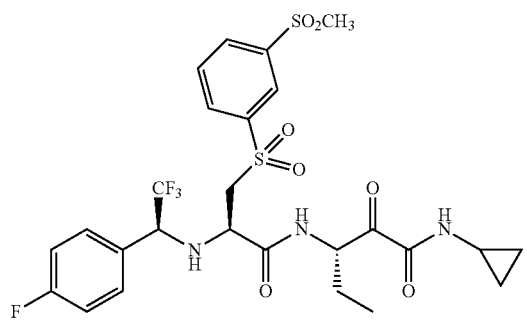

, and

Compound C

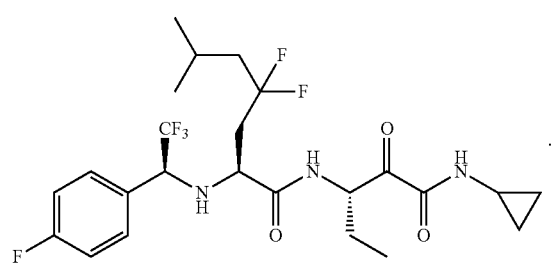

Accordingly, a preferred inhibitor is (S)—N-cyclopropyl-3-((R)-3-(cyclopropylmethylsulfonyl)-2-((S)-2,2,2-trifluoro-1-(4-fluorophenyl)ethylamino)propanamido)-2-oxopentanamide (Compound A) and its pharmaceutically acceptable salts.

Other preferred inhibitors are selected from the group consisting of:

Compound D

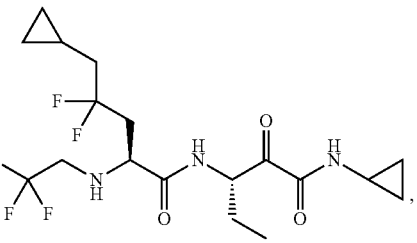

,

Compound E (structure)

, and

Compound F (structure)

.

Minimally, an S/K inhibitor inhibits both cathepsins S and K. Preferably, the cathepsin S/K inhibitor for use according to the invention is an S/B/L/K inhibitor. In some embodiments, an inhibitor may be more selective for inhibiting cathepsin S than cathepsin K, B and/or cathepsin L. In addition, the cathepsin S inhibitor can be 10-fold more selective for inhibiting cathepsin S over another cathepsin (e.g., B, K, and L). For instance, a preferred inhibitor can have an $IC_{50}$ of less than 0.1 nanomolar for cathepsin S while having an $IC_{50}$ of more than 1 nM for cathepsin F. For instance, a preferred inhibitor can have an $IC_{50}$ of less than 2 nanomolar for cathepsin S while having an $IC_{50}$ of more than 10 nM for cathepsin F. In some embodiments, the $IC_{50}$ values for inhibiting any one or all of cathepsin S, L, K and B is less than $1/5^{th}$, $1/10^{th}$, $1/20^{th}$ or $1/100^{th}$ of the $IC_{50}$ value for inhibiting Cathepsin F. In some embodiments, the $IC_{50}$ values for inhibiting cathepsin S is less than $1/5^{th}$, $1/10^{th}$, $1/20^{th}$ or $1/100^{th}$ of the $IC_{50}$ value for inhibiting any one or all of cathepsins K, B and L. Assessment of potency can be by any means. It is particularly contemplated that the potencies can be assessed according to the methods described for in vitro assays as described in the Biological Examples 1 to 5. In some embodiments, the S/K inhibitor inhibits both cathepsins S and K with $IC_{50}$ values which are each less than 1 μM, 100 nM, 10 nM, or 1 nM. In some embodiments, the S/K inhibitor inhibits each of cathepsins S, K and B with $IC_{50}$ values which are each less than 1 μM, 100 nM, 10 nM, or 1 nM. In some embodiments, the S/K inhibitor inhibits each of cathepsins S, K, and B or L with $IC_{50}$ values which are each less than 1 μM, 100 nM, 10 nM, or 1 nM. A selective cathepsin S/K inhibitor is one which has $IC_{50}$ values for inhibiting each of cathepsin S and cathepsin K which are $1/5^{th}$, $1/10^{th}$, $1/20^{th}$ or $1/100^{th}$ of the lowest $IC_{50}$ value for inhibiting any cathepsin selected from cathepsins L, B and V, and F.

BRIEF DESCRIPTION OF THE DRAWINGS

FIG. 1. Cathepsin S and B inhibitory activity for Compound A. Compound A is a covalent reversible inhibitor of cathepsins with very high potency and selectivity on multiple human cathepsin enzymes as judged by $IC_{50}$ values. Methods are similar to those set forth in the Biological Examples.

FIG. 2a: An in vitro cell assay using an activity-based probe demonstrates single digit (nM) potency in the cells. FIG. 2a shows that Compound A inhibits Cathepsin B and L activity in endothelial cells. Cellular assay using an activity-based probe demonstrates single digit (nM) potency in cells. An activity-based probe assaying using 125-I labeled DMK reagent to assess the ability of Compound A to inhibit cathepsin L and cathepsin B protease activity in cells. In this assay human umbilical vascular endothelial cells (HUVEC) are dosed with the indicated concentrations of Compound A in vitro. They are then incubated with the 125-I labeled activity probe for a short time, a cellular lysate produced, and the proteins analyzed biochemically by SDS PAGE. The gels are then imaged by autoradiography and the inhibition of protease activity, as assessed by the inhibition of activity probe binding, can be detected. FIG. 2b: Compound A inhibition of cathepsin S activity in the spleen in vivo as a function of time after dosing and plasma levels following a 10 mg/kg dose of the agent. FIG. 2b shows that Compound A inhibits Cathepsin S activity in vivo. Cathepsin inhibition is demonstrated by accumulation of biomarker in spleen following compound A dosing (10 mg/kg). The accumulation of the lip10 biomarker was tracked in spleen tissue samples taken from the treated animal. Accordingly, FIG. 2b. is based upon an assay which detects the accumulation of a proteolytic substrate of cathepsin S, the p10 fragment of invariant chain shown here as lip10, following dosing of Compound A in mice at 10 mg/kg/3 mice per time points are dosed with Compound A for the indicated times, and the spleens harvested and frozen. The level of lip10, an indicator cathepsin S inhibition is then detected using SDS PAGE and western blotting in lysates produced from the spleens. The plasma levels of the Compound A drug in the animals, an average of the three animals per time point, is shown at the bottom of the gel.

FIG. 3: Bone cancer and bone cancer pain study with Compound A. FIG. 3a: Protocol. Bone cancer pain study with Compound A. Dose groups: Vehicle, Zoledronate (100 μg/kg) positive control, Compound A (100 mg/kg, daily dosing, SC, days 7-21), 10 animals per group Control animals were injected with media (and no tumor cells) in the femur. FIG. 3b: Effects on bone destruction. FIG. 3b shows that bone destruction was attenuated by Compound A on day 14 and day 21 as compared to vehicle and also that efficacy was similar to that obtained with zoledronate. FIG. 3c shows the effects on spontaneous pain in the form of Guarding. Spontaneous pain in the form of Guarding was attenuated by Compound A on day 14 and day 21 with statistical significance as compared to vehicle or zoledronate, suggesting a direct analgesic effect; this readout is the key pain endpoint in this model and the most directly applicable to the spontaneous pain seen in human bone cancer. FIG. 3d shows the effects on flinching as measured at days 1, 7, 14, and 21. Spontaneous Pain in the form of Flinching was attenuated by Compound A on day 14 and day 21 with statistical significance, as compared to vehicle.

FIG. 4a: Compound A pharmacokinetic profile in mice and rats. FIG. 4b. Single dose pharmacokinetics in the mouse following intravenous (1 mg/kg) and oral doses (5 mg/kg). Plasma concentration values vs. time. The data indicate that Compound A has the potential for once daily dosing.

FIG. 5. Cathepsin inhibitory profiles for Compound A, Compound B, and Compound C. All human enzymes with the exception of CatK HuRab. This is a humanized rabbit cathepsin K enzyme where the key amino acids in the active site of rabbit cathepsin K have been converted to match the amino acids found in the active site of human cathepsin K. The remainder of the enzyme is rabbit. Methods are as set forth in the Examples.

In FIG. 6, the pitting of the bone is shown and indicated from samples in the study arm with 66.1 cancer cells in the bone and dosed with vehicle control only, which is due to ostelytic activity induced by the presence of the 66.1 cancer cells in the bone.

FIG. 7 shows that the indicated compounds were tested for their efficacy in blocking the resorption activity of human osteoclasts in vitro. Compounds of the present invention were added to cultured human differentiated bone marrow-derived osteoclasts cultured on bovine bone slices allowing them to resorb bone. Tartrate-resistant acid phosphatase 5b activity (TRACP 5b) was measured in the culture medium as an index of the number of osteoclasts formed in each well, and C-terminal cross-linked telopeptides of type 1 collagen (CTX) was measured in the culture medium to quantitate bone resorption. Compounds of the present invention were shown to block the resorption of bone as measured by the resorption index, which is calculated by dividing the obtained CTX values with the TRACP 5b values. The irreversible protease inhibitor E64 as well as the reversible specific cathepsin K protease inhibitor odanacatib were included as assay controls.

DETAILED DESCRIPTION OF THE INVENTION

Figure 2:
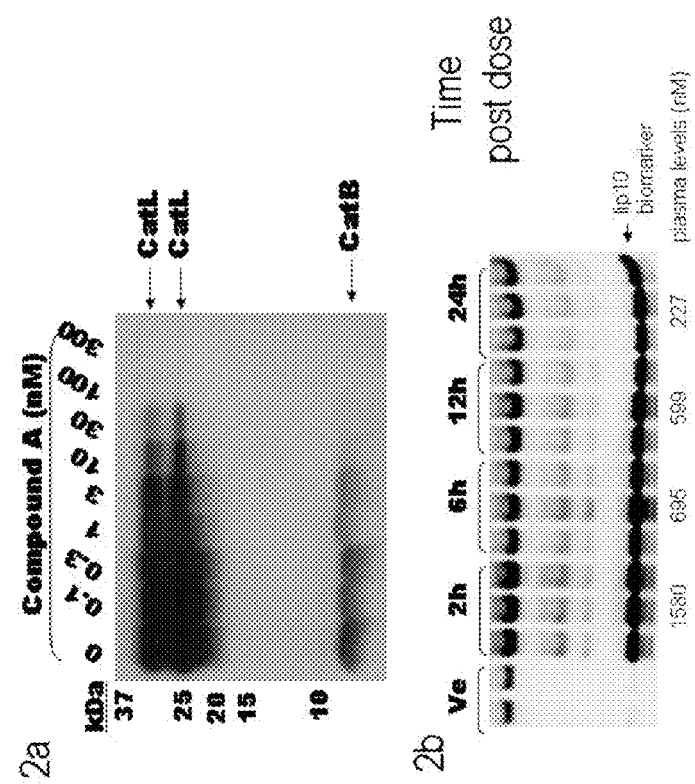
FIG. 2. Cathepsin S and B Inhibition by Compound A.

Definitions:

Unless otherwise stated, the following terms used in the specification and claims are defined for the purposes of this Application and have the following meanings.

"Alicyclic" means a moiety characterized by arrangement of the carbon atoms in closed non-aromatic ring structures e.g., cycloalkyl as defined herein.

"Alkyl" represented by itself means a straight or branched, saturated aliphatic radical containing one to eight carbon atoms, unless otherwise indicated e.g., alkyl includes methyl, ethyl, propyl, isopropyl, butyl, sec-butyl, isobutyl, tert-butyl, and the like.

"Alkylene", unless indicated otherwise, means a straight or branched, saturated aliphatic, divalent radical having the number of one to six carbon atoms, e.g., methylene (—CH₂—), ethylene (—CH₂CH₂—), trimethylene (—CH₂CH₂CH₂—), tetramethylene (—CH₂CH₂CH₂CH₂—) 2-methyltetramethylene (—CH₂CH(CH₃)CH₂CH₂—), pentamethylene (—CH₂CH₂CH₂CH₂CH₂—), and the like.

"Alkylsulfonyl" means —SO₂R radical where R is alkyl as defined herein e.g., methylsulfonyl, ethylsulfonyl, and the like.

"Alkylsulfonylamino" means —NHSO₂R radical where R is alkyl as defined herein e.g., methylsulfonylamino, ethylsulfonylamino, and the like.

"Alkoxy" refers to a —OR radical where R is an alkyl group as defined above e.g., methoxy, ethoxy, and the like.

"Alkoxyalkyl" means a linear monovalent hydrocarbon radical of one to six carbon atoms or a branched monovalent hydrocarbon radical of three to six carbons substituted with at least one alkoxy group, preferably one or two alkoxy groups, as defined above, e.g., 2-methoxy-ethyl, 1-, 2-, or 3-methoxypropyl, 2-ethoxyethyl, and the like.

"Animal" includes humans, non-human mammals (e.g., dogs, cats, rabbits, cattle, horses, sheep, goats, swine, deer, and the like) and non-mammals (e.g., birds, and the like).

"Aromatic" refers to a moiety wherein the constituent atoms make up an unsaturated ring system, all atoms in the ring system are sp² hybridized and the total number of pi electrons is equal to 4n+2.

"Biologic" means a therapeutic agent originally derived from living organisms for the treatment or management of a disease. Examples include, but are not limited to, proteins (recombinant and plasma derived), monoclonal or polyclonal, humanized or murine antibodies, toxins, hormones, and the like. Biologics are currently available for the treatment of a variety of diseases such as cancer, rheumatoid arthritis, and hemophilia.

"Cycloalkyl" refers to a monovalent saturated monocyclic ring containing three to eight ring carbon atoms e.g., cyclopropyl, cyclobutyl, cyclopentyl, cyclohexyl, and the like.

"Cycloalkylalkyl" refers to a -(alkylene)-R radical where R is cycloalkyl as defined above e.g., cyclopropylmethyl, cyclobutylethyl, cyclobutylmethyl, and the like.

"Disease" specifically includes any unhealthy condition of an animal or part thereof and includes an unhealthy condition that may be caused by, or incident to, medical or veterinary therapy applied to that animal, i.e., the "side effects" of such therapy.

"Halo" refers to fluoro or chloro.

"Haloalkyl" refers to alkyl as defined above substituted by one or more, for example from one to thirteen, preferably from one to seven, "halo" atoms, as such terms are defined in this Application. Haloalkyl includes monohaloalkyl, dihaloalkyl, trihaloalkyl, perhaloalkyl and the like e.g. chloromethyl, dichloromethyl, difluoromethyl, trifluoromethyl, 2,2,2-trifluoroethyl, perfluoroethyl, 2,2,2-trifluoro-1,1-dichloroethyl, and the like.

"Haloalkylene" means alkylene radical as defined above wherein one to four, preferably one or two hydrogen atoms in the alkylene chain has(have) been replaced by fluorine atom(s).

"Haloalkoxy" refers to a —OR radical where R is haloalkyl group as defined above e.g., trifluoromethoxy, 2,2,2-trifluoroethoxy, difluoromethoxy, and the like.

"Hydroxy" means —OH radical. Unless indicated otherwise, the compounds of the invention containing hydroxy radicals include protected derivatives thereof. Suitable protecting groups for hydroxy moieties include benzyl and the like.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Isomers" mean compounds of Formula (I) having identical molecular formulae but differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center that has two enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mix ture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992). It is understood that the names and illustration used in this Application to describe compounds of Formula (I) are meant to be encompassed all possible stereoisomers.

"Optional" or "optionally" or "may be" means that the subsequently described event or circumstance may or may not occur, and that the description includes instances where the event or circumstance occurs and instances in which it does not. For example, the phrase "wherein the aromatic ring in $R^a$ is optionally substituted with one or two substituents independently selected from alkyl" means that the aromatic ring may or may not be substituted with alkyl in order to fall within the scope of the invention.

"Pathology" of a disease means the essential nature, causes and development of the disease as well as the structural and functional changes that result from the disease processes.

"Pharmaceutically acceptable" means that which is useful in preparing a pharmaceutical composition that is generally safe, and neither biologically nor otherwise undesirable and includes that which is acceptable for veterinary use as well as human pharmaceutical use.

"Pharmaceutically acceptable salts" means salts of compounds of Formula (I) which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methylsulfonic acid, ethanesulfonic acid, 1,2-ethanedisulfonic acid, 2-hydroxy-ethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

The present invention also includes prodrugs of a compound of Formula (I). Prodrug means a compound that is convertible in vivo by metabolic means (e.g. by hydrolysis) to a compound of Formula (I). For example, an ester of a compound of Formula (I) containing a hydroxy group may be convertible by hydrolysis in vivo to the parent molecule. Alternatively an ester of a compound of Formula (I) containing a carboxy group may be convertible by hydrolysis in vivo to the parent molecule. Suitable esters of compounds of Formula (I) containing a hydroxy group, are for example acetates, citrates, lactates, tartrates, malonates, oxalates, salicylates, propionates, succinates, fumarates, maleates, methylene-bis-βp-hydroxynaphthoates, gentisates, isethionates, di-p-toluoyltartrates, methylsulphonates, ethanesulphonates, benzenesulphonates, p-toluenesulphonates, cyclohexylsulphamates and quinates. Suitable esters of compounds of Formula (I) containing a carboxy group, are for example those described by Leinweber, F. J. *Drug Metab. Res.*, 1987, 18, page 379. An especially useful class of esters of compounds of Formula (I) containing a hydroxy group, may be formed from acid moieties selected from those described by Bundgaard et al., *J. Med. Chem.*, 1989, 32, pp 2503-2507, and include substituted (aminomethyl)-benzoates, for example, dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

"Protected derivatives" means derivatives of compounds of Formula (I) in which a reactive site or sites are blocked with protecting groups. Protected derivatives of compounds of Formula (I) are useful in the preparation of compounds of Formula (I) or in themselves may be active cathepsin S inhibitors. A comprehensive list of suitable protecting groups can be found in T. W. Greene, *Protective Groups in Organic Synthesis*, 3rd edition, John Wiley & Sons, Inc. 1999.

"Therapeutically effective amount" means that amount which, when administered to an animal for treating a disease, is sufficient to effect such treatment for the disease.

"Treatment" or "treating" means any administration of a compound of the present invention and includes:

(1) preventing the disease or condition from occurring in an animal which may be predisposed to the disease but does not yet experience or display the pathology or symptomatology of the disease, (2) inhibiting the disease in an animal that is experiencing or displaying the pathology or symptomatology of the disease (i.e., arresting further development of the pathology and/or symptomatology), or (3) ameliorating the disease in an animal that is experiencing or displaying the pathology or symptomatology of the diseased (i.e., reversing the pathology and/or symptomatology).

The expression "wherein the phenyl, pyridinyl or alicyclic ring in $R^5$ is optionally substituted with one, two, or three $R^a$ independently, or two $R^b$ and one $R^c$, or one $R^c$ "in the definition of $R^5$ in the compound of Formula (I) means that all the aromatic and alicyclic rings within the scope of $R^5$ whether directly or indirectly attached (e.g., $R^5$ is cycloalkylalkyl, -alkylene-X—$R^9$ where X is as defined in the Summary of the Invention and $R^9$ is aryl, aralkyl, etc, . . . ) are optionally substituted with $R^a$, or $R^b$ and $R^c$, or $R^c$ alone.

Preferred Embodiments

I. Certain compounds of Formula (I) within the broadest scope set forth in the Summary of the Invention are preferred for use according to the invention. For example:

(A) A preferred group of compounds for use according to the invention is that wherein:

$R^1$ is hydrogen or methyl, preferably hydrogen;

$R^2$ is cyclopropyl, (1) Within the above preferred group (A) and more preferred group contained therein, a more preferred group of compounds is that wherein $R^3$ is hydrogen and $R^4$ is alkyl, preferably methyl, ethyl, propyl or butyl, more preferably $R^4$ is ethyl or propyl.

(2) Within the above preferred group (A) and more preferred group contained therein, a more preferred group of compounds is that wherein $R^4$ is cycloalkylalkyl, preferably cyclobutylmethyl or cyclopropylmethyl.

(3) Within the above preferred group (A) and more preferred group contained therein, a more preferred group of compounds is that wherein $R^3$ is alkyl, preferably methyl or ethyl and $R^4$ is alkyl, preferably methyl, ethyl, propyl or butyl, more preferably $R^4$ is methyl. Preferably, $R^3$ and $R^4$ are methyl.

(i) Within the above preferred groups (A) and A(1-3) and more preferred groups contained therein, a more preferred group of compounds is that wherein $R^6$ is haloalkyl, preferably, difluoromethyl, trifluoromethyl, 2,2,2-trifluoroethyl, 1,1,2,2,2-pentafluoroethyl, 1,1,2,2,3,3,3-heptafluoropropyl and $R^7$ is hydrogen.

(ii) Within the above preferred groups (A) and A(1-3) and more preferred groups contained therein, a more preferred group of compounds is that wherein $R^6$ is haloalkyl, preferably, trifluoromethyl, difluoromethyl, 2,2,2-trifluoroethyl, or 1,1,2,2,2-pentafluoroethyl, $R^7$ is hydrogen, and $R^8$ is phenyl optionally substituted with one, two, or three $R^e$. Preferably $R^8$ is phenyl, 4-fluorophenyl, 2,3-, 2,4-, 2,5-, 2,6-, 3,4,- or 3,5-difluorophenyl. More preferably, $R^6$ is trifluoromethyl and $R^8$ is phenyl, 4-fluorophenyl, 2,3-, 2,4-, 2,5-, 2,6-, 3,4, or 3,5-difluorophenyl, preferably 2,4-difluorophenyl.

(iii) Within the above preferred groups (A) and A(1-3) and more preferred groups contained therein, a more preferred group of compounds is that wherein $R^6$ and $R^7$ are hydrogen and $R^8$ is phenoxy-$CF_2$— wherein the phenoxy is optionally substituted with one, two, or three $R^e$. Preferably the phenoxy is 4-fluorophenoxy.

(a) Within the above preferred groups (A), A(1-3), and A(1-3) (i-iii), and more preferred groups contained therein, an even more preferred group of compounds is that wherein $R^5$ is cycloalkylalkyl optionally substituted with one, two, or three $R^a$ independently selected from alkyl or halo or an $R^c$.

(b) Within the above preferred groups (A), A(1-3), and A(1-3) (i-iii) and more preferred groups contained therein, an even more preferred group of compounds is that wherein $R^5$ is haloalkyl preferably 2,2-dichloroethyl, 3,3,3-trifluoropropyl, 2,2-trifluoromethylethyl, or 2,2,2-trifluoroethyl.

(c) Within the above preferred groups (A), A(1-3), and A(1-3) (i-iii) and more preferred groups contained therein, an even more preferred group of compounds is that wherein $R^5$ is haloalkyl, preferably 2,2-difluoro-alkyl, 2,2-difluoro-4-methylpentyl, 2,2-difluoropentyl, and 2,2-difluoroethyl, 2,2-difluoropropyl, 2,2-difluorobutyl. In some embodiments wherein $R^5$ is haloalkyl, the preferred configuration of the carbon to which $R^5$ is attached is (S).

(d) Within the above preferred groups (A), A(1-3), and A(1-3) (i-iii), and more preferred groups contained therein, an even more preferred group of compounds is that wherein $R^5$ is -(alkylene)-S(O)$_2$—$R^9$ where $R^9$ is alkyl, preferably $R^5$ is methylsulfonylmethyl, ethylsulfonylmethyl, propyl-1-sulfonylmethyl, 2-methylpropylsulfonylmethyl, 2-methyl-sulfonylethyl, or 2-ethylsulfonylethyl.

(e) Within the above preferred groups (A), A(1-3), and A(1-3) (i-iii), and more preferred groups contained therein, an even more preferred group of compounds is that wherein $R^5$ is -(alkylene or haloalkylene)-S(O)$_2$—$R^9$ where $R^9$ is phenyl, phenylalkyl, pyridinyl, or pyridinyl alkyl optionally substituted with one, two, or three $R^a$ independently selected from alkyl, haloalkyl, alkoxy, hydroxy, haloalkoxy, or halo; or optionally substituted with one or two $R^b$ independently selected from hydrogen, alkyl, haloalkyl, alkoxy, hydroxy, haloalkoxy, halo, and one $R^c$ selected from —SO$_2$R$^{11}$ (where $R^{11}$ is alkyl).

(f) Within the above preferred groups (A), A(1-3), and A(1-3) (i-iii), and more preferred groups contained therein, an even more preferred group of compounds is that wherein $R^5$ is -(alkylene)-S(O)$_2$—$R^9$ where $R^9$ is cycloalkylalkyl, preferably $R^5$ is cyclopropylmethylsulfonylmethyl.

(g) Within the above preferred groups (A), A(1-3), and A(1-3) (i-iii), and more preferred groups contained therein, $R^5$ is ethylsulfonylmethyl, 2-methysulfonylethyl, 2-methylpropylsulfonylmethyl, benzenesulfonylmethyl, 2-phenylsulfonylethyl, phenylsulfonylmethyl, phenylmethanesulfonylmethyl, 2-phenylmethanesulfonylethyl, 4-tert-butylphenylmethanesulfonylmethyl, 2-fluorophenylmethanesulfonylmethyl, 3-fluorophenylmethanesulfonylmethyl, 4-fluorophenylmethanesulfonylmethyl, 2-chlorophenylmethanesulfonylmethyl, 3-chlorophenylmethanesulfonylmethyl, 4-chlorophenylmethanesulfonylmethyl, 2-methoxyphenylmethanesulfonylmethyl, 4-methoxyphenylmethanesulfonylmethyl, 2-trifluoromethoxyphenylmethanesulfonylmethyl, 3-trifluoromethoxyphenylmethanesulfonyl-methyl, 4-trifluoromethoxyphenylmethanesulfonylmethyl, 2-trifluoromethylphenyl-methanesulfonylmethyl, 3-trifluoromethylphenylmethanesulfonylmethyl, 4-trifluoromethylphenylmethanesulfonylmethyl, 2-methylphenylmethanesulfonylmethyl, 3-methylphenylmethanesulfonylmethyl, 4-methylphenylmethanesulfonylmethyl, 2-(4-trifluoromethoxy-benzenesulfonyl)ethyl, 2-(3-trifluoromethoxybenzenesulfonyl)ethyl, 2-(2-trifluoromethoxybenzenesulfonyl)-ethyl, 2-difluoromethoxyphenylmethanesulfonylmethyl, 3-difluoromethoxyphenylmethanesulfonylmethyl, 4-difluoromethoxyphenylmethanesulfonylmethyl, 2-(4-difluoromethoxybenzenesulfonyl)ethyl, 2-(2-difluoromethoxybenzenesulfonyl)ethyl, 2-(3-difluoromethoxybenzenesulfonyl)ethyl, 3-chloro-2-fluorophenyl methanesulfonylmethyl, 3,5-dimethylphenyl methanesulfonylmethyl, 2,5-difluorophenyl methanesulfonylmethyl, 2,6-difluorophenyl methanesulfonylmethyl, 2,3-difluorophenyl methanesulfonylmethyl, 3,4-difluorophenyl methanesulfonylmethyl, 2,4-difluorophenyl methanesulfonylmethyl, 2,5-dichlorophenyl methanesulfonylmethyl, 3,4-dichlorophenyl methanesulfonylmethyl, 2,6-dichlorophenyl methanesulfonylmethyl, 2-fluoro-3-methylphenyl methanesulfonylmethyl, 4-fluoro-2-trifluoromethoxyphenyl-methanesulfonylmethyl, 2-fluoro-6-trifluoromethylphenyl-methanesulfonylmethyl, 2-fluoro-3-trifluoromethyl phenylmethanesulfonylmethyl, 2-fluoro-4-trifluoromethyl phenylmethanesulfonylmethyl, 2-fluoro-5-trifluoromethyl phenylmethanesulfonylmethyl, 4-fluoro-3-trifluoromethyl phenylmethanesulfonylmethyl, 2-chloro-5-trifluoromethylphenylmethanesulfonylmethyl, 2,4,6-trifluorophenyl-methanesulfonylmethyl, 2,4,5-trifluorophenylmethanesulfonylmethyl, 2,3,4-trifluorophenylmethanesulfonylmethyl, 2,3,5-trifluorophenylmethanesulfonylmethyl, 2,5,6-trifluorophenylmethanesulfonylmethyl, 3,4,5-trimethoxyphenylmethanesulfonylmethyl. In some of these embodiments, the preferred stereochemistry at the carbon to which $R^5$ is attached is (R), and the preferred stereochemistry at the carbons to which $R^4$ and $R^6$ are attached is (S). In certain other embodiments, the preferred configuration of the carbon to which $R^5$ is attached is (S). In some embodiments, wherein $R^5$ is haloalkyl, the preferred configuration of the carbon to which $R^5$ is attached is (S).

Within the groups above, the stereochemistry at the carbon to which $R^6$ is attached is (S) and the preferred stereochemistry at the carbons to which $R^4$ and $R^5$ are attached is (R).

(A) Yet another preferred group of compounds of Formula (I) is that wherein $R^6$ is haloalkyl, preferably, difluoromethyl, trifluoromethyl, 2,2,2-trifluoroethyl, or 1,1,2,2,2-pentafluoroethyl and $R^7$ or $R^8$ is hydrogen.

In other embodiments of any of the above the recited haloalkyl members are each a C1-C6 or C1-C3 haloalkyl member; in further embodiments of the above, each recited cycloalkyl member is a cyclopropyl.

In other embodiments of any of the above, the compound for use according to the invention is a compound of Formula I wherein each recited alkyl and alkylene member is a C1 to C6 member. In still further embodiments of any of the above, the compound for use according to the invention is a compound of Formula I wherein each recited alkyl and alkylene member is a C1 to C3 member. In still further of these embodiments, any of the above the recited haloalkyl members are each a C1-C6 or C1-C3 haloalkyl member.

Similarly, in other embodiments of any of the above the recited haloalkyl members are each a C1-C6 or C1-C3 haloalkyl member.

Representative compound for use according to the invention is a compound of Formula (I) where $R^1$ is hydrogen, $R^6$ is trifluoromethyl and other groups are as defined in Table I below are:

| Stereochem. at *C,C,*C | $R^2$ | $R^3$ | $R^4$ | $R^5$ | $R^7$ | $R^8$ |
|---|---|---|---|---|---|---|
| (S,R,S) | cyclopropyl | H | n-propyl | cyclopropylmethanesulfonylmethyl | H | 4-F-phenyl |
| (S,R,S) | cyclopropyl | H | n-propyl | pyridin-3-ylmethanesulfonyl-methyl | H | 4-F-phenyl |
| (R,R,S) | cyclopropyl | H | n-propyl | cyclopropylmethanesulfonylmethyl | H | 4-F-phenyl |
| (*S,**R) | cyclopropyl | | | cyclopropylmethanesulfonylmethyl | H | 4-F-phenyl |
| (*S,**R) | cyclopropyl | $CH_3$ | $CH_3$ | cyclopropylmethanesulfonylmethyl | H | 4-F-phenyl |
| (S,R,S) | cyclohexyl | H | ethyl | cyclopropylmethanesulfonylmethyl | H | 4-F-phenyl |
| (*S,R,*S) | cyclopropyl | H | ethyl | 3-trifluoromethylsulfonylmethyl | H | 4-F-phenyl |
| (*S,R,*S) | cyclopropyl | H | ethyl | 3-methylsulfonylbenzylsulfonylmethyl | H | 4-F-phenyl |
| (*S,R,*S) | cyclopropyl | H | ethyl | cyclopropylmethanesulfonylmethyl | H | 4-F-phenyl |
| (*S,R,*S) | cyclopropyl | H | ethyl | 4-trifluorophenylsulfonylmethyl | H | 4-F-phenyl |
| (*S,R,*S) | cyclopropyl | H | ethyl | 4-methylsulfonylphenylsulfonylmethyl | H | 4-F-phenyl |
| (*S,S,*S) | cyclopropyl | H | ethyl | 2-cyclohexylethyl | H | 4-F-phenyl |
| (S,*S) | cyclopropyl | H | ethyl | benzyloxymethyl | H | 4-F-phenyl |
| (*S,S,*S) | cyclopropyl | H | ethyl | 2-phenylsulfonylethyl | H | 4-F-phenyl |
| (*S,R,*S) | cyclopropyl | H | ethyl | 3,5-trifluoromethylphenylsulfonylmethyl | H | 4-F-phenyl |
| (*S,S,*S) | cyclopropyl | H | ethyl | 2,2-difluoro-3-phenylpropyl | H | 4-F-phenyl |
| (*S,S,*S) | cyclopropyl | H | ethyl | 2,2,2-trifluoroethyl | H | 4-F-phenyl |
| (*S,R,*S) | cyclopropyl | H | ethyl | 3-methoxyphenylsulfonylmethyl | H | 4-F-phenyl |
| (*S,R,*S) | cyclopropyl | H | ethyl | 4-methoxyphenylsulfonylmethyl | H | 4-F-phenyl |
| (*S,R,*S) | cyclopropyl | H | ethyl | 2-methoxyphenylsulfonylmethyl | H | 4-F-phenyl |
| (*S,R,*R) | cyclopropyl | H | ethyl | phenylsulfonylmethyl | H | 4-F-phenyl |
| (*S,S,*S) | cyclopropyl | H | ethyl | 2-methanesulfonylethyl | H | 4-F-phenyl |
| (*S,S,*S) | cyclopropyl | H | ethyl | 2,2-difluoro-4-methylpentyl | H | 4-F-phenyl |
| (*S,S,*S) | cyclopropyl | H | ethyl | phenylsulfonylaminomethyl | H | 4-F-phenyl |
| (*S,S,*S) | cyclopropyl | H | ethyl | isopropylsulfonylaminomethyl | H | 4-F-phenyl |
| (*S,S,*S) | cyclopropyl | H | ethyl | methylsulfonylaminomethyl | H | 4-F-phenyl |
| (*S,S,*S) | cyclopropyl | H | ethyl | 2-(4-trifluoromethyl-phenylsulfonyl)ethyl | H | 4-F-phenyl |
| (*S,S,*S) | cyclopropyl | H | ethyl | 2-(4-trifluoromethylphenylsulfanyl)ethyl | H | 4-F-phenyl |
| (*S,S,*S) | cyclopropyl | H | ethyl | 2-methylsulfinylethyl | H | 4-F-phenyl |
| (*S,S,*S) | cyclopropyl | H | ethyl | 3-phenylpropyl | H | 4-F-phenyl |
| (*S,S,*S) | cyclopropyl | H | ethyl | 2-(4-methylsulfonylphenylsulfonyl)ethyl | H | 4-F-phenyl |
| (*S,S,*S) | cyclopropyl | H | ethyl | 2-chlorobenzyl | H | 4-F-phenyl |
| (*S,**R) | cyclopropyl | $CH_3$ | $CH_3$ | 2-$CH_3SO_2$phenylmethane-sulfonylmethyl | H | 4-F-phenyl |
| (S,R,S) | cyclopropyl | H | ethyl | phenylsulfonylmethyl | H | 4-F-phenyl |
| (*S,**R) | cyclopropyl | $CH_3$ | $CH_3$ | 3-$CH_3SO_2$phenylmethanesulfonylmethyl | H | 4-F-phenyl |
| (S,R,S) | cyclopropyl | H | ethyl | 2-cyclopropylmethanesulfonylethyl | H | 4-F-phenyl |
| (*S,**R) | cyclopropyl | $CH_3$ | $CH_3$ | 4-$CH_3SO_2$phenylmethanesulfonylmethyl | H | 4-F-phenyl |
| (*S,R,*S) | cyclopropyl | H | ethyl | phenylylsulfonylmethyl | H | phenyl |

General Synthetic Scheme

Compounds of this invention can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCh Publishers Inc., 1989). These schemes are merely illustrative of some methods by which the compounds of this invention can be synthesized, and various modifications to these schemes can be made and will be suggested to one skilled in the art having referred to this disclosure. See U.S. Pat. No. 7,488,848 which is incorporated by reference in its entirety with respect to the compounds disclosed therein and the disclosed methods of making the compounds as well as their disclosed chemical physical and biological activities and disclosed methods of testing for enzyme inhibition.

The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "*Protective Groups in Organic Chemistry*" John Wiley and Sons, 1999.

Compounds of Formula (I) where $R^1$, $R^2$, $R^3$, $R^4$, $R^5$, $R^6$ and $R^8$ are as defined in the Summary of the Invention and $R^7$ is hydrogen can be prepared by proceeding as in the following Reaction Scheme 1 below.

Scheme 1

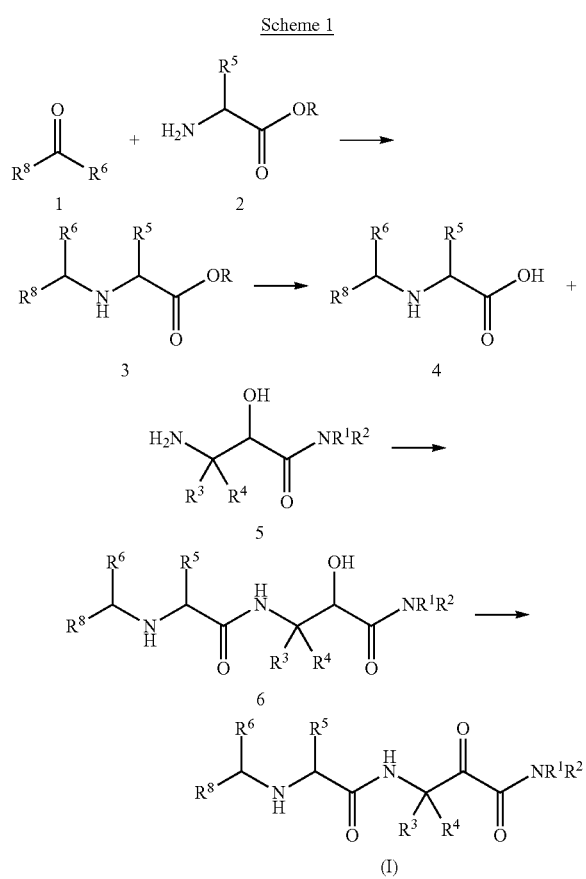

Reaction of a ketone of formula 1 where $R^6$ and $R^8$ are as defined in the Summary of the Invention with an α-amino ester of formula 2 where R is a carboxy protecting group, preferably an alkyl group, preferably methyl, and $R^5$ is as defined in the Summary of the Invention under reductive amination reaction conditions provide a compound of formula 3. The reaction is carried out in the presence of a suitable dehydrating agent such as $TiCl_4$, magnesium sulfate, isopropyl trifluoroacetate, in the presence of a base such as diisopropylethylamine, pyridine, and the like and in a suitable organic solvent such as methylene chloride to give an imine. The imine is reduced with a suitable reducing agent such as sodium borohydride, sodium cyanoborohydride, and the like in a suitable organic solvent such as methanol, ethanol, and the like.

Compounds of formula 1 such as 2,2,2-trifluoromethylacetophenone and 2,2,2,4'-tetrafluoroacetophenone are commercially available. Others can be prepared by methods well known in the art. α-Amino esters of formula 2 can be prepared by methods well known in the art e.g., PCT Applications Publication Nos. WO 03075836, WO 00/55144, WO 01/19816, WO 02/20485, WO 03/029200, U.S. Provisional Application No. 60/422,337, U.S. Pat. No. 6,353,017B1, U.S. Pat. No. 6,492,662B1, U.S. Pat. No. 6,353,017 B1 and U.S. Pat. No. 6,525,036B1, U.S. Pat. No. 6,229,011B1, U.S. Pat. No. 6,610,700, the disclosures of which are incorporated herein by reference in their entirety.

Hydrolysis of the ester group in compound 3 provides a compound of formula 4. The hydrolysis conditions depend on the nature of the protecting group. For example, when R is alkyl the hydrolysis is carried out under aqueous basic hydrolysis reaction conditions to give the corresponding acid of formula 4. The reaction is typically carried out with cesium carbonate, lithium hydroxide, and the like in an aqueous alcohol such as methanol, ethanol, and the like.

Compound 4 is then reacted with an α-hydroxyketoamide of formula 5 to give a compound of Formula 6. The reaction is typically carried out in the presence of a suitable coupling agent e.g., benzotriazole-1-yloxytrispyrrolidinophosphonium hexafluorophosphate (PyBOP®), O-benzotriazol-1-yl-N,N,N',N'-tetramethyl-uronium hexafluorophosphate (HBTU), O-(7-azabenzotriazol-1-yl)-1,1,3,3-tetramethyl-uronium hexafluorophosphate (HATU), 1-(3-dimethylaminopropyl)-3-ethylcarbodiimide hydrochloride (EDC), or 1,3-dicyclohexyl-carbodiimide (DCC), optionally in the presence of 1-hydroxy-benzotriazole (HOBT), and a base such as N,N-diisopropylethylamine, triethylamine, N-methylmorpholine, and the like. The reaction is typically carried out at 20 to 30° C., preferably at about 25° C., and requires 2 to 24 h to complete. Suitable reaction solvents are inert organic solvents such as halogenated organic solvents (e.g., methylene chloride, chloroform, and the like), acetonitrile, N,N-dimethylformamide, ethereal solvents such as tetrahydrofuran, dioxane, and the like.

Alternatively, the above coupling step can be carried out by first converting 4 into an active acid derivative such as succinimide ester and then reacting it with an α-hydroxyketoamide of formula 5. The reaction typically requires 2 to 3 h to complete. The conditions utilized in this reaction depend on the nature of the active acid derivative. For example, if it is an acid chloride derivative of 4, the reaction is carried out in the presence of a suitable base (e.g. triethylamine, diisopropylethylamine, pyridine, and the like). Suitable reaction solvents are polar organic solvents such as acetonitrile, N,N-dimethylformamide, dichloromethane, or any suitable mixtures thereof. Compounds of formula 5 can be prepared by methods well known in the art e.g., they can be prepared by the procedures described in PCT application publication No. WO 02/18369, the disclosure of which is incorporated herein by reference in its entirety.

Oxidation of the hydroxyl group in compound 6 with a suitable oxidizing agent, preferably Dess-Martin Periodinane, provides a compound of Formula (I).

Alternatively, compounds of Formula (I) where $R^1$, $R^2$, $R^3$, $R^4$, $R^5$, $R^6$ and $R^8$ are as defined in the Summary of the Invention and $R^7$ is hydrogen can be prepared by proceeding as in the following Reaction Scheme 2 below.

Scheme 2

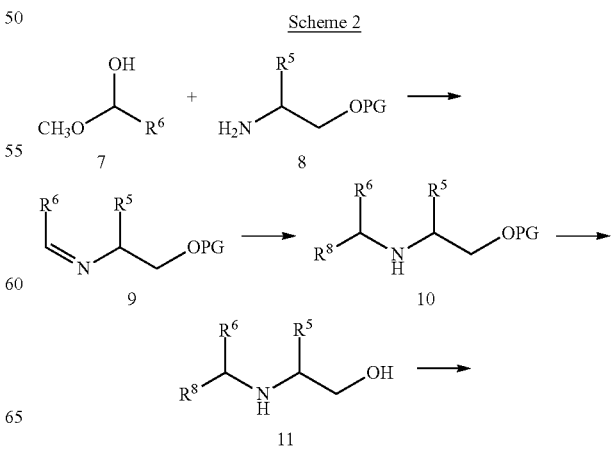

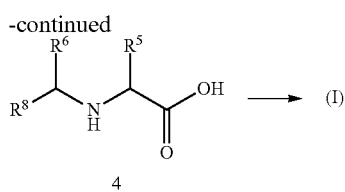

Reaction of a compound of formula 8 where $R^5$ is as defined in the Summary of the Invention and PG is a suitable oxygen protecting group with a hemiacetal of formula 7 where $R^6$ is as defined in the Summary of the Invention provides an imine compound of formula 9. Treatment of 9 with an organolithium compound of formula $R^8Li$ where $R^8$ is not hydrogen provides compound 10. Removal of the oxygen protecting group, followed by oxidation of the resulting alcohol 11 provides a compound of formula 4 which is then converted to a compound of Formula (I) as described in Scheme 1 above. Suitable oxygen protecting groups and reaction conditions for putting them on and removing them can be found in Greene, T. W.; and Wuts, P. G. M.; *Protecting Groups in Organic Synthesis*; John Wiley & Sons, Inc. 1999.

Alternatively, compounds of Formula (I) where $R^1$, $R^2$, $R^3$, $R^4$, $R^5$, $R^6$ and $R^8$ are as defined in the Summary of the Invention and $R^7$ is hydrogen can be prepared by proceeding as in the following Reaction Scheme 3 below.

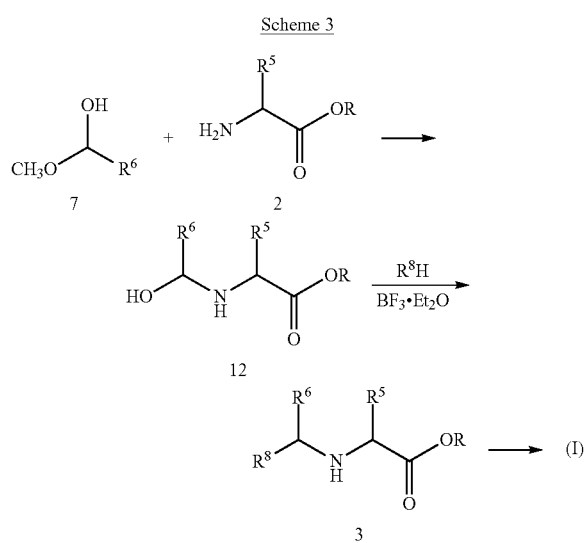

Reaction of an amino acid compound of formula 2 where R is alkyl and $R^5$ is as defined in the Summary of the Invention with a hemiacetal compound of formula 7 provides a 2-(1-hydroxy-2,2,2-trifluoroethylamino)acetate compound of formula 12. The reaction is carried out in the presence of a catalytic amount of an acid such as p-toluenesulfonic acid and in an aromatic hydrocarbon solvent such as toluene, benzene, and the like.

Treatment of 12 with a compound of formula $R^8H$ where $R^8$ is aryl or heteroaryl under Friedel-Crafts reaction conditions or trialkylaluminum in toluene provides a compound of formula 3 which is then converted to a compound of Formula (I) as described above.

Alternatively, compounds of Formula (I) where $R^1$, $R^2$, $R^3$, $R^4$, $R^5$, $R^6$ and $R^8$ are as defined in the Summary of the Invention and $R^7$ is hydrogen can be prepared by proceeding as in the following Reaction Scheme 4 below.

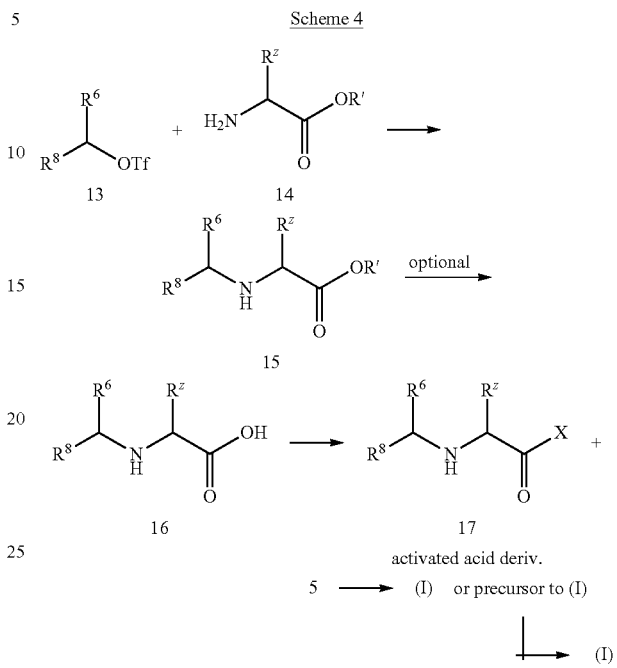

Reaction of a compound of formula 13 wherewith a compound of formula 14 where R' is hydrogen or a carboxy protecting group and $R^z$ is $R^5$ or a precursor group (e.g., -alkylene-S-trityl, -alkylene-S-alkylene-heteroaryl, and the like) to $R^5$ group provides a compound of formula 15. The reaction is carried out in a suitable organic solvent, including but not limited to, diethyl ether, tetrahydrofuran, acetonitrile, benzene, toluene, xylene, and the like, or mixtures thereof and optionally in the presence of an organic or inorganic base. Preferably, the organic base is triethylamine, pyridine, N-methylmorpholine, collidine, diisopropylethylamine, and the like. Preferably, the inorganic base is cesium carbonate, sodium carbonate, sodium bicarbonate, and the like. The reaction is optionally carried out in the presence of a drying agent such as molecular sieves. Preferably, the reaction is carried out at room temperature.

Compounds of formula 13 can be prepared by methods well known in the art. For example, a compound of formula 13 where $R^8$ is phenyl or 4-fluorophenyl and $R^6$ is trifluoromethyl can be readily prepared from commercially available 2,2,2-trifluoroacetophenone or 2,2,2,4'-tetrafluoroacetophenone respectively, by reducing the keto group to an alcoholic group by suitable reducing agent such as sodium borohydride, lithium aluminum hydride, and the like. The solvent used depends on the type of reducing agent. For example, when sodium borohydride is used the reaction is carried out in an alcoholic organic solvent such as methanol, ethanol, and the like. When lithium aluminum hydride is used the reaction is carried out in an ethereal solvent such as tetrahydrofuran, and the like. Reaction of 2,2,2-trifluoro-1-phenylethanol or 2,2,2-trifluoro-1-(4-fluorophenyl)ethanol with triflic anhydride or trifluoromethanesulfonyl chloride provides the desired compound. Compounds of formula 13 where $R^7$ and $R^8$ are hydrogen and $R^6$ is 1,1,2,2,2-pentafluoroethyl can be prepared from commercially available 2,2,3,3,3-pentafluoropropan-1-ol can as described above. Optically enriched compound of formula 15 can be obtained by reduction of the corresponding halogenated acetophenone with a suitable reducing agent such as catecholborane or $BH_3$-DMS complex in the presence of a suitable catalyst such as (S) or (R)-methyl CBS oxazaborolidine catalyst or (S) or (R)-α,α-diphenyl-2-pyrrolidine-methanol in the presence of BBN to provide chiral alcohol which is then converted to compound 13 as described above. Compounds of formula 14 are either commercially available or they can be prepared by methods well known in the art.

Removal of the carboxy protecting group from a compound of formula 15 where R' is a protecting group provides a compound of formula 16. The conditions used to remove the carboxy protecting group depend on the nature of the carboxy protecting group. For example, if $R^1$ is alkyl, it is removed under basic hydrolysis reaction conditions utilizing aqueous base such as aqueous lithium hydroxide, sodium hydroxide, and the like in an alcoholic solvent such as methanol, ethanol, and the like. Additionally, if the $R^z$ group in compound 14 is a precursor group to $R^5$, it can be converted to $R^5$ prior or after the ester hydrolysis step.

Compound 15 (where R' is hydrogen) or 16 is then converted to an activated acid derivative 17 (X is a leaving group) and which upon reaction with an aminoacetonitrile compound of formula 5 provides a compound of Formula (I) when $R^z$ is $R^5$ or a precursor compound to (I) when $R^z$ is a precursor group to $R^5$. The activated acid derivative can be prepared and then reacted with compound 5 in a stepwise manner or the activated acid derivative can be generated in situ in the presence of compound 5. For example, if the activated acid is acid halide it is first prepared by reacting 16 with a halogenating agent such as thionyl chloride, oxalyl chloride and the like and then reacted with compound 5. Alternatively, the activated acid derivative is generated in situ by reacting compound 16 and 5 in the presence of a suitable coupling agent e.g., benzotriazole-1-yloxytrispyrrolidinophosphonium hexafluorophosphate (PyBOP®), O-benzotriazol-1-yl-N,N,N',N'-tetramethyl-uronium hexafluorophosphate (HBTU), O-(7-azabenzotriazol-1-yl)-1,1,3,3-tetramethyl-uronium hexafluorophosphate (HATU), 1-(3-dimethylaminopropyl)-3-ethylcarbodiimide hydrochloride (EDC), 1,3-dicyclohexyl-carbodiimide (DCC), an the like, optionally in the presence of 1-hydroxybenzotriazole (HOBT), and in the presence of a base such as N,N-diisopropylethylamine, triethylamine, N-methylmorpholine, and the like. Suitable reaction solvents are inert organic solvents such as halogenated organic solvents (e.g., methylene chloride, chloroform, and the like), acetonitrile, N,N-dimethylformamide, ethereal solvents such as tetrahydrofuran, dioxane, and the like. If $R^z$ is a precursor group to $R^5$, it is converted to $R^5$ group to provide a compound of Formula (I) e.g, conversion of -alkylene-S-alkylene-heteroaryl to -alkylene-$SO_2$-alkylene-heteroaryl under oxidation reaction conditions. Alternatively, $R^z$ can be converted to $R^5$ to yield compound 4 prior to amide bond formation with compound 5.

A compound of Formula (I) can be converted to other compounds of Formula (I). For example:

A compound of Formula (I) containing a hydroxy group may be prepared by de-alkylation/benzylation of an alkoxy/benzyloxy substituent; those containing an acid group, by hydrolysis of an ester group; and those containing a cyano, by displacement of a bromine atom on the corresponding compounds of Formula (I). A compound of Formula (I) containing a cyano group can be converted to a corresponding carboxy containing compound by hydrolysis of the cyano group. The carboxy group, in turn, can be converted to an ester group.

A compound of Formula (I) can be prepared as a pharmaceutically acceptable acid addition salt by reacting the free base form of the compound with a pharmaceutically acceptable inorganic or organic acid. Alternatively, a pharmaceutically acceptable base addition salt of a compound of Formula (I) can be prepared by reacting the free acid form of the compound with a pharmaceutically acceptable inorganic or organic base. Inorganic and organic acids and bases suitable for the preparation of the pharmaceutically acceptable salts of compounds of Formula (I) are set forth in the definitions section of this Application. Alternatively, the salt forms of the compounds of Formula (I) can be prepared using salts of the starting materials or intermediates.

The free acid or free base forms of the compounds of Formula (I) can be prepared from the corresponding base addition salt or acid addition salt form. For example, a compound of Formula (I) in an acid addition salt form can be converted to the corresponding free base by treating with a suitable base (e.g., ammonium hydroxide solution, sodium hydroxide, and the like). A compound of Formula (I) in a base addition salt form can be converted to the corresponding free acid by treating with a suitable acid (e.g., hydrochloric acid, etc).

The N-oxides of compounds of Formula (I) can be prepared by methods known to those of ordinary skill in the art. For example, N-oxides can be prepared by treating an unoxidized form of the compound of Formula (I) with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds of Formula (I) can be prepared from the N-oxide of an appropriate starting material.

Compounds of Formula (I) in unoxidized form can be prepared from N-oxides of compounds of Formula (I) by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g., acetonitrile, ethanol, aqueous dioxane, or the like) at 0 to 80° C.

Prodrug derivatives of the compounds of Formula (I) can be prepared by methods known to those of ordinary skill in the art (e.g., for further details see Saulnier et al. (1994), *Bioorganic and Medicinal Chemistry Letters*, Vol. 4, p. 1985). For example, appropriate prodrugs can be prepared by reacting a non-derivatized compound of Formula (I) with a suitable carbamylating agent (e.g., 1,1-acyloxyalkylcarbonochloridate, para-nitrophenyl carbonate, or the like).

Protected derivatives of the compounds of Formula (I) can be made by means known to those of ordinary skill in the art. A detailed description of the techniques applicable to the creation of protecting groups and their removal can be found in T. W. Greene, *Protecting Groups in Organic Synthesis*, 3rd edition, John Wiley & Sons, Inc. 1999.

Compounds of the present invention may be conveniently prepared or formed during the process of the invention, as solvates (e.g. hydrates). Hydrates of compounds of the present invention may be conveniently prepared by recrystalisation from an aqueous/organic solvent mixture, using organic solvents such as 1,4-dioxane, tetrahydrofuran or methanol.

Compounds of Formula (I) can be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diasteromeric derivatives of compounds of Formula (I), dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, *Enantiomers, Racemates and Resolutions*, John Wiley & Sons, Inc. (1981). Methods of making and preparing compounds of the invention are also disclosed in PCT Patent Application Publication No. WO2006/102243, published Sep. 28, 2006; and PCT Patent Application Publication No. WO2010/056877, published on May 20, 2010; both of which are incorporated herein by reference in their entirety with respect to such methods.

Pharmacology and Utility

The compounds of the invention are selective inhibitors of cathepsin S and also cathepsins K, B, and/or L, and are useful for treating diseases and conditions related to bone cancer, including metastatic bone cancer. In some embodiments, the metastatic cancer is a multiple myeloma, a melanoma, a head and neck cancer, a breast cancer, a prostate cancer, a kidney cancer or a lung cancer. In some embodiments, the compounds are administered to patients in need thereof to reduce metastasis to bone, reduce bone cancer pain, or reduce bone erosion, bone loss or damage (e.g., microfractures, bone distortion, disruption of bone periosteum), associated with the cancer or its metastasis to bone. In some embodiments accordingly the invention provides methods of treating metastatic cancer bone pain (e.g., inflammatory pain, neuropathic pain, nerve pain, or breakthrough pain) in patients in need thereof. In some embodiments, the pain is due to bone microfactures, bone distortion, mechanical stress, or disruption of the periosteum with stretching and entrapment of nerves associated with the cancer. In some embodiments, the cancer is an osteolytic metastasis or an osteoblastic metastasis. Compounds for use according to the invention have inhibitory activity for cathepsin S cathepsin K and optionally other cathepsins, including cathepsins B, and L. Accordingly, Compound A is particularly preferred.

The cysteine protease inhibitory activities of the compounds of Formula (I) can be determined by methods known to those of ordinary skill in the art. Suitable in vitro assays for measuring protease activity and the inhibition thereof by test compounds are known. Typically, the assay measures protease-induced hydrolysis of a peptide-based substrate. Details of suitable assays for measuring protease inhibitory activity are set forth in Biological Examples 1-6, infra. Compound D has a very favorable cathepsin inhibitory profile respective of the intended use in treating bone cancer and bone cancer pain.

Compound E has been tested on a subset of enzymes with the methods already described. The results are: cathepsin S $IC_{50}$=332 pM. Cathepsin B, L, and V all IC50<100 nM. Cathepsins B, L, and V were tested at one concentration, 100 nM, and they all provided 98% or greater inhibition of the enzymes.

Compound F has been tested on the following enzymes with the methods already described. The $IC_{50}$ values were as follows: Cathepsin S=340 pM; Cathepsin K (huRab)=28 nM; Cathepsin B=2.5 nM; Cathepsin F=74 nM; Cathepsin L=300 pM; Cathepsin V<250 pM.

Compound D was tested with the following results: Cathepsin S $IC_{50}$=267 pM; Cathepsin B $IC_{50}$=23 nM; Cathepsin L $IC_{50}$<100 nM (75% inhibition at a single data point of 100 nM); Cathepsin V $IC_{50}$<100 nM (63% inhibition at a single data point of 100 nM).

Administration and Pharmaceutical Compositions

In general, compounds of Formula (I) will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. For example, therapeutically effective amounts of a compound of Formula (I) may range from about 10 micrograms per kilogram body weight (μg/kg) per day to about 100 milligram per kilogram body weight (mg/kg) per day, typically from about 100 μg/kg/day to about 10 mg/kg/day. Accordingly, in some embodiments, the therapeutically effective amount is from 1 to 100 mg/kg/day. Therefore, a therapeutically effective amount for an 80 kg human patient may range from about 1 mg/day to about 8 g/day, typically from about 1 mg/day to about 800 mg/day. In general, one of ordinary skill in the art, acting in reliance upon personal knowledge and the disclosure of this Application, will be able to ascertain a therapeutically effective amount of a compound of Formula (I) for treating a given disease. In accordance with typical body weights and dosage regimes, in some embodiments, unit dosages may be in an amount from 1 mg to 100 mg, 100 mg to 1 g, or from 1 to 10 g.

The compounds of Formula (I) can be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula (I) in combination with at least one pharmaceutically acceptable excipient. Acceptable excipients are non-toxic, aid administration, and do not adversely affect the therapeutic benefit of the active ingredient. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, and the like). Preferred liquid carriers, particularly for injectable solutions, include water, saline, aqueous dextrose and glycols.

The amount of a compound of Formula (I) in the composition may vary widely depending upon the type of formulation, size of a unit dosage, kind of excipients and other factors known to those of skill in the art of pharmaceutical sciences.

In general, a composition of a compound of Formula (I) for treating a given disease will comprise from 0.01% w to 90% w, preferably 5% w to 50% w, of active ingredient with the remainder being the excipient or excipients. Preferably the pharmaceutical composition is administered in a single unit dosage form for continuous treatment or in a single unit dosage form ad libitum when relief of symptoms is specifically required. Representative pharmaceutical formulations containing a compound of Formula (I) are described below.

EXAMPLES

The present invention is further exemplified, but not limited by, the following examples.

Synthesis of Compounds

Example 1

Synthesis of N-cyclopropyl-3S-{4-methanesulfonyl-2S-[2,2,2-trifluoro-1S-(4-fluoro-phenyl)-ethylamino]-butyrylamino}-2-oxo-pentanamide

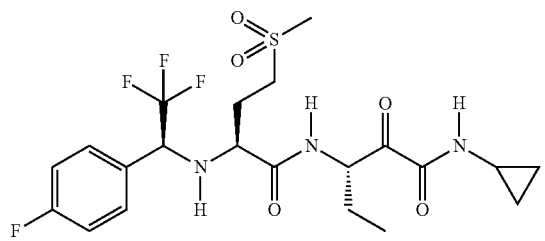 [SMILES: CC[C@H](NC(=O)[C@H](CCS(C)(=O)=O)N[C@@H](c1ccc(F)cc1)C(F)(F)F)C(=O)C(=O)NC1CC1]

(S)Methyl2-amino-4-methylsulfanylbutyrate hydrochloride (750 mg, 3.76 mmol) and 2,2,2-trifluoro-1-(4-fluorophenyl)-ethanone (721 mg, 3.76 mmol) was dissolved in methanol (15 mL) and then potassium carbonate (1.04 g, 7.52 mmol) was added to the solution. The mixture was stirred at 55° C. for 23 hours and then concentrated to dryness on a rotovap. The residue was combined with toluene (20 mL) and the mixture was concentrated to dryness on a rotovap. The residue was combined with acetonitrile (10 mL) and the mixture was stirred at approximately −30° C. Zinc borohydride, prepared by adding a 1M zinc chloride solution in ether (5.64 mL) to a mixture of sodium borohydride (427 mg, 11.28 mmol) stirring in ether (10 mL) and then stirring this mixture 19 hours, was added and the reaction stirred for approximately 7 hours at reduced temperature and then an additional 16 hours at room temperature. The reaction mixture was quenched with 1N HCl, diluted with ethyl acetate, and washed with brine (2×50 mL). The organic layer was dried and concentrated to provide 2S-[2,2,2-trifluoro-1S-(4-fluorophenyl)ethylamino]-4-methylsulfanylbutyric acid (1.15 g) as solid.

2S-[2,2,2-Trifluoro-1S-(4-fluorophenyl)ethylamino]-4-methylsulfanylbutyric acid (150 mg, 0.46 mmol), cyclopropyl 3S-amino-2-hydroxypentanamide hydrochloride (106 mg, 0.51 mmol), EDC (132 mg, 0.69 mmol) and HOBt (75 mg, 0.55 mmol) were combined in DCM (10 mL) and the mixture was stirred at room temperature while N-methylmorpholine (0.253 mL, 2.3 mmol) was added. The mixture was stirred for 2 hours and 15 minutes and then diluted with ethyl acetate. The mixture was washed with sodium bicarbonate solution (2×35 mL) and the organic layer was dried and concentrated to provide N-cyclopropyl-2-hydroxy-3S-{4-methanesulfonyl-2S-[2,2,2-trifluoro-1S-(4-fluoro-phenyl)-ethylamino]-butyrylamino}-pentanamide (188 mg) as a white solid.

N-Cyclopropyl-2-hydroxy-3S-{4-methanesulfonyl-2S-[2,2,2-trifluoro-1S-(4-fluoro-phenyl)-ethylamino]-butyrylamino}-pentanamide (188 mg, 0.39 mmol) was dissolved in 1-methyl-2-pyrrolidinone (5 mL) and the solution was stirred at room temperature while an aqueous solution of oxone (5 mL, 434 mg, 0.71 mmol) was added. The mixture was stirred for 1 hour and 45 minutes and then diluted with ethyl acetate. The mixture was washed with brine (3×25 mL) and the organic layer was dried and concentrated. The residue was dissolved in 1-methyl-2-pyrrolidinone (5 mL) and then Dess-Martin periodinane (232 mg, 0.55 mmol) was added to the solution. The reaction was allowed to proceed for 1 hour and then the solution was diluted with ethyl acetate. The mixture was washed with sodium bicarbonate solution (3×30 mL) and the organic layer was dried and concentrated. The residue was combined with ether and triturated to form a solid. The mixture was scraped and filtered to provide N-cyclopropyl-3S-{4-methanesulfonyl-2S-[2,2,2-trifluoro-1S-(4-fluoro -phenyl)-ethylamino]-butyrylamino}-2-oxo-pentanamide (114 mg) as a white solid (mp 152.5-153.5° C.). LC-MS 510(M+H).

Example 2

Synthesis of Compound D

Preparation of a Compound of Formula I in which $R^1$ is hydrogen, $R^2$ is cyclopropyl, $R^3$ is hydrogen, $R^4$ is ethyl, $R^5$ is $CH_2CF_2CH_2$cyclopropyl, $R^6$ and $R^7$ are hydrogen and $R^8$ is 4-fluorophenoxy-$CF_2$—.

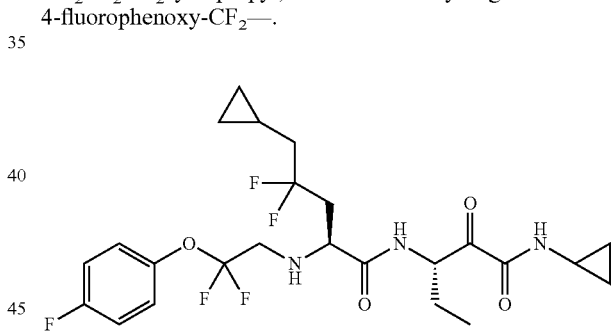

To a solution of (2S)-5-cyclopropyl-N-((3S)-1-(cyclopropylamino)-2-hydroxy-1-oxopentan-3-yl)-2-(2,2-difluoro-2-(4-fluorophenoxy)ethylamino)-4,4-difluoropentanamide (190 mg, 0.36 mmol) in N-methylpyrrolidine (4 ml) was added Dess-Martin periodinane reagent (216 mg, 0.51 mmol, 1.4 eq). The mixture was stirred for 4 hours at room temperature, then added to saturated aqueous sodium bicarbonate (50 ml) containing sodium thiosulfate (1.5 g). The mixture was stirred for 1 hour, filtered, the solid material washed with water, then dried in a vacuum oven at 40° C. using phosphorus pentoxide as a drying agent, yielding (S)-5-cyclopropyl-N-((S)-1-(cyclopropylamino)-1,2-dioxopentan-3-yl)-2-(2,2-difluoro-2-(4-fluorophenoxy)ethylamino)-4,4-difluoropentanamide 144 mg (76%).

$^1$H NMR (d6-DMSO; 400MHz): δppm 8.65 (1H), 8.38 (1H), 7.35 (m, 4H), 4.90 (m, 1H), 3.48 (m, 1H), 3.22 (m, 1H), 3.05 (m, 1H), 2.72 (m, 1H), 2.65 (m, 1H), 2.35 -2.00 (m), 1.55 (m, 1H), 1.35 (m), 0.90-0.42 (m, 10H), 0.60-0.40 (m, 6H), 0.12 (m, 2H). LC/MS: retention time; t=20.01 min Mass: (M+H)$^+$ 520.

Example 3

Synthesis of 2-oxo-3(S)-{3-(pyridin-3-ylmethanesulfonyl)-2(R)-[2,2,2-trifluoro-1(S)(4-fluorophenyl)ethylamino]-propionylamino}hexanoic acid cyclopropylamide Step 1

Catecholborane (19.4 mL, 182 mmol) in dichloromethane (15 mL) was added to a dichloromethane solution of S-methyl CBS oxazaborolidine (13 mL, 13 mmol) and 2,2,2,4'-tetrafluoroacetopheone (18.2 mL, 130.13 mmol) dropwise at −78° C. in 30 min. The reaction mixture was stirred at −78° C. overnight. The reaction mixture was quenched with 4N HCl (13 mL) in dioxane at −78° C., warmed up to room temperature and the solvent was removed under reduced pressure. 10 % $NaHSO_3$ solution (200 mL) was added to concentrate and the aqueous layer was extracted by hexane. The organic layer was washed by water and dried with $MgSO_4$. Solvent was removed under the reduced pressure to give 2,2,2-trifluoro-1(R)-(4-fluorophenyl)-ethanol (20 g) as colorless oil (90% e.e.).

Step 2

NaH (11.87 g, 296.7 mmol) was added to $Et_2O$ (700 mL) at 0° C. under $N_2$ followed by addition of an $Et_2O$ solution of 2,2,2-trifluoro-1(R))-4-fluorophenyl)ethanol (44.3 g, 228.2 mmol). The reaction mixture was stirred for 10 min at 0° C. then 1 hr at room temperature. Trifluoromethanesulfonyl chloride (50 g, 296.7 mmol) in $Et_2O$ was added at 0° C. under $N_2$ and the reaction mixture was stirred 10 min at 0° C. then 3 h at room temperature. The solvent was removed under the reduced pressure and $H_2O$ (100 mL) was added slowly. The aqueous layer was extracted by hexane and the combined organic layer was dried over $MgSO_4$. The solvent was removed under the reduced pressure to give trifluoromethanesulfonic acid 2,2,2-trifluoro-1(R)-(4-fluorophenyl)ethyl ester (70 g) as colorless oil.

Step 3

2(R)-Amino-3-tritylsulfanylpropionic acid (78 g, 214.6 mmol) was dissolved in $CH_2Cl_2$ and DIPEA (112 mL, 643.8 mmol) was added and the reaction mixture was stirred for 10 min at room temperature. Trifluoromethanesulfonic acid 2,2,2-trifluoro-1(R)-(4-fluorophenyl)ethyl ester (70 g, 214.6 mmol) in $CH_2Cl_2$ was added and the reaction mixture was stirred overnight at room temperature. Solvent was removed under the reduced pressure and the residue was dissolved in $Et_2O$ and washed with 1N HCl, brine and dried over $MgSO_4$. Solvent was removed give 2(R)-[2,2,2-trifluoro-1(S)-(4-fluorophenypethylamino]-3-tritylsulfanylpropionic acid (90 g) as a yellow solid.

Step 4

2(R)-[2,2,2-trifluoro-1(S)-(4-fluorophenyl)ethylamino]-3-tritylsulfanylpropionic acid (5.4 g, 10 mmol) was dissolved in $CH_2Cl_2$ and TFA (3.1 mL, 40 mmol) was added at 0° C. under $N_2$. $Et_3SiH$ (3.2 mL, 20 mmol) was added at 0° C. under $N_2$ and the reaction mixture was warmed up to room temperature. After stirring for 2 h, the solvent was removed under the reduced pressure and the residue was dissolved in 1N NaOH (120 mL). The aqueous layer was extracted with hexane. To the aqueous solution dioxane (120 mL), 3-picolyl chloride hydrochloride (1.97 g, 12 mmol), and tris(2-carboxyethyl) phosphine hydrochloride (280 mg, 1 mmol) were added. The reaction mixture was stirred at room temperature overnight. Dioxane was removed under the reduced pressure. The aqueous solution was adjusted to pH 3 and was extracted with ethyl acetate. The combined organic extracts were dried over $MgSO_4$, filtered and concentrated under the reduced pressure to give 3-(pyridin-3-ylmethanesulfanyl)-2(R)-[2,2,2-trifluoro-1(S)- (4-fluorophenyl)-ethylamino]propionic acid which was used in the next step without further purification.

Step 5

To a solution of 3-(pyridin-3-ylmethanesulfanyl)-2(R)-[2,2,2-trifluoro-1(S)-(4-fluorophenyl)-ethylamino]propionic acid in methanol (10 mL), an aqueous solution of OXONE® (4.68 g, 15 mmol in 10 mL $H_2O$) was added. The reaction mixture was stirred at room temperature. After 2 h, solvent was removed under reduced pressure. The aqueous layer was extracted with ethyl acetate and the combined organic extracts were was washed with brine and dried with $MgSO_4$ and filtered The filtrate was concentrated under the reduced pressure to give 3-(pyridin-3-ylmethanesulfonyl)-2-(R)[2,2,2-trifluoro-1((S)-(4-fluorophenyl)ethylamino]propionic acid which was used in the next step without further purification.

Step 6

A mixture of 3-(pyridin-3-ylmethanesulfonyl)-2-(R)[2,2,2-trifluoro-1(S)-(4-fluorophenyl)ethylamino] propionic acid (420 mg, 1 mmol), 3(S)-amino-2-hydroxyhexanoic acid cyclopropylamide (186 mg, 1 mmol) prepared as described in PCT application publication No. WO-02/18369 as compound xiii, HBTU (455 mg, 1.2 mmol), and NMM (0.44 mL, 4 mmol) in acetonitrile was stirred at room temperature overnight. Sat. $NH_4Cl$ (10 mL) and ethyl acetate (10 mL) were added and after 20 min the aqueous layer was extracted with ethyl acetate. The combined organic extracts were washed with brine and dried with $MgSO_4$, filtered and the filtrated was concentrated under the reduced pressure to give 2-hydroxy-3(S)-{3-(pyridin-3-ylmethanesulfonyl)-2(R)[2,2,2-trifluoro-1(S)-(4-fluorophenyl)-ethylamino]propionylamino}-hexanoic acid cyclopropylamide which was used in the next step without further purification.

Step 7

To a solution of 2-hydroxy-3(S)-{3-(pyridin-3-ylmethanesulfonyl)-2(R)-[2,2,2-trifluoro-1(S)-(4-fluorophenyl)ethylamino]propionylamino }hexanoic acid cyclopropylamide (590 mg, 1 mmol) in methylene chloride, DMP was added slowly. The reaction mixture was stirred at room temperature for 30 min and then a 0.26 M $Na_2S_2O_3$ in sat. $NaHCO_3$ was added. The reaction mixture was stirred for 20 min. The aqueous layer was extracted with methylene chloride and the combined organic extracts were dried over $MgSO_4$, filtered and concentrated to give 2-oxo-3(S)-{3-(pyridin-3-ylmethanesulfonyl)-2(R)-[2,2,2-trifluoro-1(S)-(4-fluorophenyl)ethylamino]-propionylamino}hexanoic acid cyclopropylamide which was purified by flash column (2% MeOH—$CH_2Cl_2$) to give pure product as a yellow solid.

$^1$H-NMR(DMSO-$d_6$): δ 0.80(m, 12H), 2.02(m, 1H), 3.3-3.7(b, 3H), 4.00(m, 1H), 4.46(m, 1H), 4.79(m, 2H), 7.25(m, 2H), 7.50(m, 21-1), 7.65(b, 1H), 7.72(d, 1H), 8.01(d, 1H), 8.71(m, 3H). LC-MS: 587(M+1), 585, (M−1), 609(M+23).

Proceeding as described above but substituting 3-picolyl chloride with cyclopropylmethyl bromide provided 2-oxo-3 (S)-{3-(cyclopropylmethanesulfonyl)-2(R)-[2,2,2-trifluoro-1(S)-(4-fluorophenyl)ethylamino]-propionylamino}hexanoic acid cyclopropylamide.

$^1$H-NMR(DMSO$_6$): δ 0.32-0.41 (m, 2H), 0.53-0.67 (m, 6H), 0.81(t, J=7.2Hz, 3H), 1:06-1.38 (m, 4H), 1.52-1.61 (m, 1H), 2.69-2.76 (m, 1H), 2.98 (dd, J=2.8Hz, J=14.8Hz,1H), 3.19 (dd, J=8Hz, J=14Hz, 1H), 3.28-3.50 (m, 3H), 3.82-3.88 (m, 1H), 4.37 (quint, J=7.6Hz, 1H), 4.70-4.76 (m, 1H), 7.22 (t, J=8.4Hz, 2H), 7.43 (dd, J=5.6Hz, J=8.4Hz, 2H), 8.51 (d, J=7.2Hz, 1H), 8.73 (d, J=5.2Hz, 1H). LC-MS: 550(M+1), 548, (M−1).

Proceeding as described above but replacing 3(S)-amino-2-hydroxyhexanoic acid cyclopropylamide hydrochloride with cyclopropyl3S-amino-2-hydroxypentamide hydrochloride would provide (S)—N-cyclopropyl-2-oxo-3-((R)-3-((pyridin-3-ylmethyl)sulfonyl)-2-(((S)-2,2,2-trifluoro-1-(4-fluorophenyl)ethyl)amino)propanamido)pentanamide (Compound F).

Example 4

Synthesis of (S)—N-cyclopropyl-3-((R)-3-((cyclopropylmethyl)sulfonyl)-2-(((S)-2,2,2-trifluoro-1-(4-fluorophenyl)ethyl)amino)propanamido)-2-oxopentanamide (Compound A)

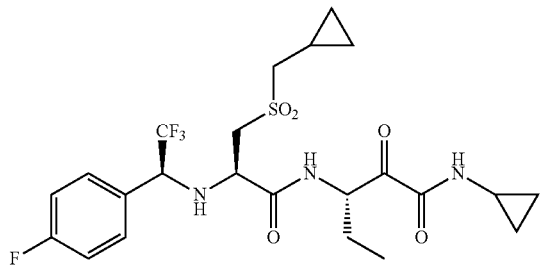 [SMILES: CC[C@H](NC(=O)[C@H](CS(=O)(=O)CC1CC1)N[C@@H](c1ccc(F)cc1)C(F)(F)F)C(=O)C(=O)NC1CC1]

Step 1

A suspension of 2,2,2,4'-tetrafluoroacetophenone (48 g; 250 mmol) and (R)-methyl2-amino-3-((cyclopropylmethyl)thio)propanoate hydrochloride (56.4 g; 250 mmol) in isopropanol (IPA; 1100 mL) was added potassium carbonate (69.1 g; 500 mmol; 200 mole %) and the mixture heated at 50-60° C. under a nitrogen atmosphere. After 46 h, the reaction mixture was filtered hot through a pad of celite that was prewashed with hot IPA. The filter was washed with hot IPA (2x) and the combined filtrate and washes were distilled to about 90% of the original volume. Acetonitrile (ACN) was added and the solvent was distilled. This process was repeated two more times with ACN and the product was evaporated to dryness. Potassium (R,Z)-3-((cyclopropylmethyl)thio)-2-((2,2,2-trifluoro-1-(4-fluorophenyl)ethylidene)-amino)propanoate (87 g; 90%) was obtained after drying under high vacuum (1 mm Hg) for 2 hours. This material was used in the next reaction without further purification.

Step 2

Anhydrous zinc(II) chloride (51.1 g; 375 mmol) was suspended in 1,2-dimethoxyethane (DME; 500 mL) under nitrogen and stirred for 2 days at ambient temperature. The reaction mixture was cooled in an ice bath then lithium borohydride (16.3 g; 750 mmol; 200 mol % relative to $ZnCl_2$) was added in portions. The resulting mixture containing the zinc(II) borohydride was stirred for 24 h under nitrogen.

Crude potassium (R,Z)-3-((cyclopropylmethyl)thio)-2-((2,2,2-trifluoro-1-(4-fluorophenyl)ethylidene)-amino)propanoate [89 g; 225 mmol] was dissolved in acetonitrile (1100 mL) and cooled to −40° C. using a dry-ice/acetonitrile bath. The $Zn(BH_4)_2$ suspension prepared as described above was added dropwise to the acetonitrile solution over a 1-hour period, maintaining the internal temperature below −40° C. After the addition was complete, the reaction mixture was maintained at −40 to −50° C. for 7 hours then allowed to warm up to 10° C.

The mixture was cooled to −10° C. and quenched by the slow addition of 1N aqueous HCl until the solution was at pH 1. The reaction mixture was diluted with MTBE (~1 L) and the layers were separated. The aqueous phase was extracted with MTBE (2x) and the combined organic phases were washed with water (2x), saturated aqueous sodium chloride. The organic phase was concentrated in vacuo to a small volume, dissolved in additional MTBE (~1.5 L), washed with water, saturated aqueous sodium chloride, and dried ($MgSO_4$) and concentrated to dryness to give 76.3 g (86.8%) of the crude (R)-3-((cyclopropylmethyl)thio)-2-(((S)-2,2,2-trifluoro-1-(4-fluorophenyl)ethyl)amino)propanoic acid. Proton NMR showed this material to contain about 7-10% of the (R,R)-diastereomer.

The crude product (76.3 g; 217 mmol) was dissolved in MTBE (400 mL) and cooled in an ice-water bath. A solution of (S)-phenethanamine (26.3 g; 217 mmol; 100 mole %) in MTBE (100 mL) was added slowly dropwise and the mixture stirred overnight at ambient temperature. The solid was filtered, washed with cold MTBE and hexane, then dried in a vacuum oven to give 57.0 g (55.0%; 46.5% from 2,2,2,4'-tetrafluoroacetophenone). The solid was recrystallized from hot acetonitrile (200 mL). The solution was filtered, washed with cold ACN and hexane then dried in vacuo to give 52.2 g of the salt. The salt was converted to the free acid using 10% aqueous potassium hydrogensulfate and MTBE. Evaporation of the MTBE layer provided an oil which was crystallized by trituration. Drying in vacuo gave 38.8 g (44% over 3 steps) of (R)-3-((cyclopropylmethyl)thio)-2-(((S)-2,2,2-trifluoro-1-(4-fluorophenyl)ethyl)amino)propanoic acid containing about 3.8% of the (R,R)-diastereomer. LC-MS, positive ion mode: m/z=352 $[M+H]^+$; negative ion mode: m/z=350 $[M-H]^-$, 100%.

Step 3

A solution of (R)-3-((cyclopropylmethyl)thio)-2-(((S)-2,2,2-trifluoro-1-(4-fluorophenyl)ethyl)amino)-propanoic acid [22.6 g; 64.3 mmol] in a mixture of toluene (120 mL), ethyl acetate (12 mL) was added sodium tungstate dihydrate (424 mg; 1.29 mmol; 2 mole %); tetra-n-butylammonium hydrogensulfate (870 mg; 2.57 mmol; 4 mole %) and phenylphosphinic acid (200 mg; 1.29 mmol; 2 mol %). The resulting mixture was treated with 30% hydrogen peroxide (20 mL; 9.8 mmol; 300 mole %) at ambient temperature. After the addition was complete, the mixture was stirred for 2.5 h at ambient temperature. The reaction mixture was diluted with a 10% aqueous sodium thiosulfate solution (800 mL) and ethyl acetate (800 mL). The biphasic solution was cooled in an ice-water bath and acidified with concentrated HCl to pH 2. The layers were separated and the organic phase was washed with water and saturated aqueous sodium chloride. The organic phase was dried ($MgSO_4$) and concentrated in vacuo to give an oil. The residue was triturated with hexane (3x), followed by hexane (150 mL) and methyl t-butylether (MTBE; 5 mL) was added. The resulting oily mixture was cooled in an ice bath, resulting in the formation of a solid. The solid was then stirred for 3 days at ambient temperature, filtered and washed with hexane and dried in a vacuum oven to give 22 g (89%) of (R)-3-((cyclopropylmethyl)sulfonyl)-2-(((S)-2,2,2-trifluoro-1-(4-fluorophenyl)ethyl)amino)propanoic acid. LC-MS, positive ion mode: m/z=384 $[M+H]^+$, 208 $[M-C_8F_4H_5+2H]^+$, 100%; negative ion mode: m/z=382 $[M-H]^-$, 100%.

Step 4

A solution of (R)-3-((cyclopropylmethyl)sulfonyl)-2-(((S)-2,2,2-trifluoro-1-(4-fluorophenyl)ethyl)-amino)propanoic acid [56.7 g; 148 mmol] in dichloromethane (1800 mL) was treated with HATU (67.5 g; 178 mmol; 120 mol %) and stirred at ambient temperature for 10 minutes. N-cyclopropyl 3S-amino-2-hydroxypentanamide hydrochloride (30.9 g; 148 mmol) was then added and the mixture stirred at ambient temperature for 10 minutes, then cooled in an ice water bath. N,N-Diisopropylamine (DIPEA; 77 mL; 57 g; 441 mmol; 298 mole %) was added slowly, along with DMF (25 mL). The resulting mixture was stirred in the ice bath for 30 minute then overnight at ambient temperature. The dichloromethane was removed by distillation and the residue partitioned between ethyl acetate and a 10% aqueous solution of potassium hydrogensulfate. The layers were separated and the organic phase was washed with water, aqueous sodium bicarbonate, water and finally aqueous sodium chloride. The organic phase was dried (MgSO$_4$) and concentrated to a wet solid. The solid was slurried in diethyl ether with stirring for a few hours. The gelatinous solid was filtered, washing with hexane to facilitate drying. The wet solid was dried on the filter providing a solid, which was ground to a powder. The solid was suspended in a solution of 5% MTBE in hexane and stirred overnight to provide a finely-powdered solid. The slurry was cooled in an ice-water bath and filtered and dried in a vacuum oven at 40° C. to give 63.3 g (79.6%) of (3S)—N-cyclopropyl-3-((R)-3-((cyclopropylmethyl)sulfonyl)-2-(((S)-2,2,2-trifluoro-1-(4-fluorophenyl)-ethyl)amino)propanamido)-2-hydroxypentanamide. LC-MS, positive ion mode: m/z=538 [M+H]$^+$ (100%); negative ion mode: m/z=536 [M–H]$^-$ (100%). Methods for the preparation of starting materials are disclosed in U.S. Pat. No. 7,488,848, which is incorporated herein by reference in its entirety with respect to such methods.

Step 5

To a stirred suspension of (3S)—N-cyclopropyl-3-((R)-3-((cyclopropylmethyl)sulfonyl)-2-(((S)-2,2,2-trifluoro-1-(4-fluorophenyl)ethyl)amino)propanamido)-2-hydroxypentanamide [63.2 g; 118 mmol] in a mixture of acetonitrile (1150 mL) and dichloromethane (1150 mL) previously cooled in a cold water bath, was added DMP (69.86 g; 164.7 mmol; 140 mol %) in portions. The resulting reaction mixture was stirred for 4 h at ambient temperature. The reaction mixture was concentrated in vacuo to distill about 1 L of solvent and the remaining solution was added to a mixture of 1M aqueous sodium thiosulfate (800 mL) and saturated aqueous sodium bicarbonate (800 mL). Ethyl acetate (1.6 L) was added and the biphasic mixture stirred for 1.5 h. The layers were separated and the organic phase was washed with water, a mixture of water and a solution of sodium chloride in water and finally a solution of sodium chloride in water. The organic phase was dried (MgSO$_4$) and concentrated to a wet solid which was suspended in hexane. The resulting slurry was stirred overnight, filtered and the solid was washed with hexane. Drying provided 53.6 g (85%) of the title compound. Recrystallization of this material alone with 4 g of crude (S)—N-cyclopropyl-3-((R)-3-((cyclopropylmethyl)sulfonyl)-2-(((S)-2,2,2-trifluoro-1-(4-fluorophenyl)ethyl)amino)propanamido)-2-oxopentanamide from another lot (57.6 g total) using hot IPA (1700 mL) gave 52 g of a white solid after washing with cold IPA and hexane, followed by drying over P$_2$O$_5$ in a vacuum oven at 40° C. LC-MS, positive ion mode: m/z=536 [M+H]$^+$ (100%); $^{19}$F-NMR (CDCl$_3$) δ, ppm: –74.54 (s); –110.09 (s).

Example 5

Synthesis of (S)—N—((S)-1-(cyclopropylamino)-1,2-dioxopentan-3-yl)-4,4-difluoro-6-methyl-2-(((S)-2,2,2-trifluoro-1-(4-fluorophenyl)ethyl)amino)heptanamide (Compound C)

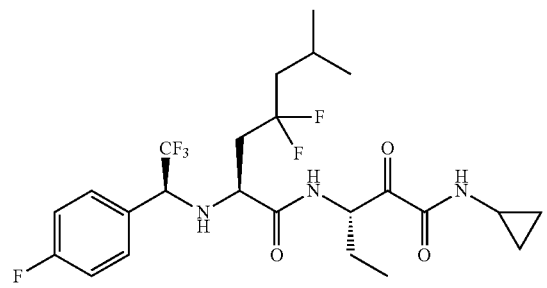 [SMILES: CC[C@H](NC(=O)[C@H](CC(F)(F)CC(C)C)N[C@@H](c1ccc(F)cc1)C(F)(F)F)C(=O)C(=O)NC1CC1]

Step 1

A suspension of 2,2,2,4'-tetrafluoroacetophenone (1.80 g; 9.37 mmol) and (S)-methyl 2-amino-4,4-difluoro-6-methyl-heptanoate hydrobromide (2.72 g; 9.37 mmol) in isopropanol (IPA; 50 mL) under a nitrogen atmosphere, was added potassium carbonate (2.59 g; mmol; 200 mole %) and the mixture was stirred 50° C. After 48 h, the reaction mixture was filtered hot through a pad of celite that was prewashed with hot IPA. The filter was washed with hot IPA (3×50 mL) and the combined filtrate and washes were distilled to dryness. Acetonitrile (ACN) was added and the solvent was distilled. The distillation from acetonitrile was repeated twice and the product was evaporated to dryness. Potassium (S,Z)-4,4-difluoro-6-methyl-2((2,2,2-trifluoro-1-(4-fluorophenyl)ethylidene)amino)-heptanoate (3.13 g; 82%) was used in the next reaction without further purification. Methods for the preparation of starting materials are disclosed in U.S. Pat. No. 7,893,112, which is incorporated herein by reference in its entirety with respect to such methods.

Step 2

Anhydrous zinc(II) chloride (1.92 g; 14.1 mmol) was suspended in 1,2-dimethoxyethane (DME; 15 mL) under nitrogen and stirred for 23 h at ambient temperature. Lithium borohydride (620 mg; 28.5 mmol; 202 mol % relative to ZnCl$_2$) was added. The resulting mixture containing the zinc (II) borohydride was stirred for 48 h under nitrogen.

Potassium (S,Z)-4,4-difluoro-6-methyl-2-((2,2,2-trifluoro-1-(4-fluorophenyl)ethylidene)amino)-heptanoate [3.13 g; 7.68 mmol] was dissolved in acetonitrile (80 mL) and cooled to –40 to –42° C. using a dry-ice/acetonitrile bath. The Zn(BH$_4$)$_2$ suspension prepared as described above was added dropwise to the solution of Example O over a 15-minute period, maintaining the internal temperature below –40° C. After the addition was complete, the reaction mixture was maintained at about –45° C. for 6 hours then allowed to warm slowly to ambient temperature overnight.

The mixture was cooled to –5° C. and quenched by the slow addition of 1N aqueous HCl until the solution was at pH 2 (~50 mL). The aqueous phase was extracted with MTBE (3×40 mL) and the combined organic phases were washed with water (50 mL), followed by saturated aqueous sodium chloride (50 mL). The organic phase was concentrated in vacuo and the residue was dissolved in MTBE (100 mL), washed with water (50 mL), saturated aqueous sodium chloride (50 mL), and dried (MgSO$_4$) and concentrated to dryness to give 2.89 g (83.3%) of the crude product. This material was chromatographed on silica gel, eluting with ethyl acetate/hexane, 1:4 followed by ethyl acetate/hexane, 1:2 to give 2.20 g (63.2%) of (S)-4,4-Difluoro-6-methyl-2-(((5)-2,2,2-trifluoro-1-(4-fluorophenyl)ethyl)amino)heptanoic acid. LC-MS, positive ion mode: m/z=372 [M+H]$^+$; negative ion mode: m/z=370 [M–H]$^-$ (100%).

Step 3

A solution of (S)-4,4-difluoro-6-methyl-2-(((S)-2,2,2-trifluoro-1-(4-fluorophenyl)ethy)amino)heptanoic acid [1.00 g; 2.70 mmol] in dichloromethane (30 mL) and N,N-dimethylformamide (DMF; 10 mL) was treated with HATU (1.23 g; 2.90 mmol; 120 mol %) under nitrogen followed by the addition of N-cyclopropyl 3S-amino-2-hydroxypentanamide hydrochloride (560 mg; 2.69 mmol). N-methylmorpholine (NMM; 890 µL; 819 mg; 8.09 mmol; 300 mole %) was added. The resulting mixture was stirred for 23 h overnight at ambient temperature. The reaction mixture was diluted with ethyl acetate (150 mL) and wasjed with 1N HCl (2×50 mL), water (50 mL), saturated sodium bicarbonate (50 mL), and finally a solution of saturated sodium chloride (50 mL). The organic phase was dried (MgSO$_4$) and concentrated to give 1.5 g of solid. The solid was slurried in diethyl ether with stirring for a few hours. The gelatinous solid was filtered, washing with hexane to facilitate drying. The wet solid was dried on the filter providing a solid, which was ground to a powder. The solid was suspended in a solution of 5% MTBE in hexane and stirred overnight to provide a finely-powdered solid. The slurry was cooled in an ice-water bath and filtered and dried in a vacuum oven at 40° C. to give 63.3 g (79.6%) of (2S)-N-((3S)-1-(cyclopropylamino)-2-hydroxy-1-oxopentan-3-yl)-4,4-difluoro-6-methyl-2-(((S)-2,2,2-trifluoro-1-(4-fluorophenyl)ethy)amino)heptanamide. LC-MS, positive ion mode: m/z=526 [M+H]$^+$(100%); negative ion mode: m/z=524 [M–H]$^-$; 584 [M–H+AcOH]$^-$(100%). Methods for the preparation of starting materials are disclosed in U.S. Pat. No. 7,488,848.

Step 4

To a stirred suspension of (2S)—N-((3S)-1-(cyclopropylamino)-2-hydroxy-1-oxopentan-3-yl)-4,4-difluoro-6-methyl-2-(M-2,2,2-trifluoro-1-(4-fluorophenyl)amino) heptanamide [1.59 g; 3.03 mmol] in dry dichloromethane (45 mL) under nitrogen, previously cooled in a cold water bath, was added DMP (1.71 g; 4.03 mmol; 133 mol %). The resulting reaction mixture was stirred for 5 h at ambient temperature. The reaction mixture was diluted with ethyl acetate (75 mL) and washed in sequence with 0.2M aqueous sodium thiosulfate solution (60 mL), saturated aqueous sodium bicarbonate solution (3×60 mL) and saturated aqueous sodium chloride (60 mL). The organic phase was dried (MgSO$_4$) and concentrated in vacuo. The resulting product (1.60 g) was chromatographed over silica gel, eluting with ethyl acetate/hexane, 1:4 followed by ethyl acetate/hexane, 1:3 to give 1.10 g (69.6%) of (S)—N—((S)-1-(cyclopropylamino)-1,2-dioxopentan-3-yl)-4,4-difluoro-6-methyl-2-(((S)-2,2,2-trifluoro-1-(4-fluorophenyl)ethyl)amino)heptanamide. Proton NMR showed this material to contain about 8% of the epimeric derivative. Recrystallization of this material (IPA; 7 mL) provided 320 mg (20%) of the compound free of the diastereomeric impurity according to $^{19}$F-NMR analysis: δ, ppm (CDCl$_3$): –74.57 (s); –94.23 (s); –112.44 (s); LC-MS, positive ion mode: m/z=524 [M+H]$^+$ (100%).

Example 6

Synthesis of (S)-5-cyclopropyl-N—((S)-1-(cyclopropylamino)-1,2-dioxopentan-3-yl)-4,4-difluoro-2-(((S)-2,2,2-trifluoro-1-(4-fluorophenyl)ethyl)amino) pentanamide (Compound E)

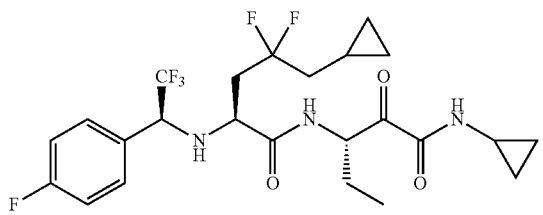 [SMILES: CC[C@H](NC(=O)[C@H](CC(F)(F)CC1CC1)N[C@@H](c1ccc(F)cc1)C(F)(F)F)C(=O)C(=O)NC1CC1]

Step 1

A solution of (S)-5-cyclopropyl-4,4-difluoro-2-(((S)-2,2,2-trifluoro-1-(4-fluorophenyl)ethyl)amino)-pentanoic acid (0.5 g; 1.35 mmol) in dry dichloromethane (16 mL) under nitrogen was treated with HOBt (228 mg; 1.49 mmol; 110 mol %), EDC hydrochloride (286 mg; 1.49 mmol; and (3S)-3-amino-N-cyclopropyl-2-hydroxypentanamide hydrochloride (311 mg; 1.49 mmol; 110 mole %). N-methylmorpholine (NMM; 210 µL; 301 mg; 2.97 mmol; 220 mole %) was added and resulting mixture was stirred for 20 h at ambient temperature. The dichloromethane was removed by distillation and the residue partitioned between ethyl acetate (50 mL) and washed in sequence with 10% aqueous citric acid (20 mL), saturated aqueous sodium bicarbonate (20 mL), and saturated aqueous sodium chloride (20 mL). The organic phase was dried (MgSO$_4$) and concentrated in vacuo to give 740 mg of the crude product which was chromatographed on silica gel (5 g), eluting with ethyl acetate/hexane, 1:2 followed by 1:1, to give 469 mg (66.2%) of (25)-5-cyclopropyl-N-((3S)-1-(cyclopropylamino)-2-hydroxy-1-oxopentan-3-yl)-4,4-difluoro-2-(((S)-2,2,2-trifluoro-1-(4-fluorophenyl)ethyl) amino)pentanamide. LC-MS, positive ion mode: m/z=524 [M+H]$^+$ (100%). Methods for the preparation of starting materials are disclosed in U.S. Pat. Nos. 7,488,848 and 7,893,112.

Step 2

To a stirred suspension of (2S)-5-cyclopropyl-N-((3S)-1-(cyclopropylamino)-2-hydroxy-1-oxopentan-3-yl)-4,4-difluoro-2-(((S)-2,2,2-trifluoro-1-(4-fluorophenyl)ethyl) amino)pentanamide [469 mg; 0.897 mmol] in a mixture of acetonitrile (3 mL) and dichloromethane (3 mL) under nitrogen, previously cooled in a cold water bath, was added DMP (494 mg; 1.17 mmol; 130 mol %). The resulting reaction mixture was stirred for 23 h at ambient temperature. The reaction mixture was diluted with ethyl acetate (25 mL) and washed in sequence with 0.2M aqueous sodium thiosulfate solution (20 mL), saturated aqueous sodium bicarbonate solution (3×20 mL) and saturated aqueous sodium chloride (20 mL). The organic phase was dried (MgSO$_4$) and concentrated in vacuo. The resulting product was chromatographed over silica gel (5 g), eluting with ethyl acetate/hexane 1:4 then 1:3 to give 330 mg of a gummy solid. This material was stirred in hexane (~7 mL) overnight and the suspension was filtered and washed with hexane (3×5 mL) to give 206 mg (44%) of Example U. Proton NMR of this sample showed a 7:2 mixture of diastereomers. Addition of acetonitrile followed by distillation of most of the solvent and addition of hexane (10 mL) give a suspension that was stirred overnight. The slurry was filtered, washed with hexane (2×2 mL) and dried to give 118 mg (20%) of (S)-5-cyclopropyl-N—((S)-1-(cyclopropylamino)-1,2-dioxopentan-3-yl)-4,4-difluoro-2-a(S)-2,2,2-trifluoro-1-(4-fluorophenyl)ethyl)amino)pentanamide as a ~10:1 mixture of diastereomers according to the $^{19}$F-NMR spectrum. LC-MS, positive ion mode: m/z=522 [M+H]$^+$, 100%; 544 [M+Na]$^+$; $^{19}$F-NMR (CDCl$_3$) δ, ppm (major isomer): −74.59 (s); −95.21 (d); −112.47 (s).

Example 7

Synthesis of (S)—N-Cyclopropyl-3-((R)-3-((3-(methylsulfonyl)phenyl)sulfonyl)-2-(((S)-2,2,2-trifluoro-1-(4-fluorophenyl)ethyl)amino)propanamido)-2-oxopentanamide (Compound B)

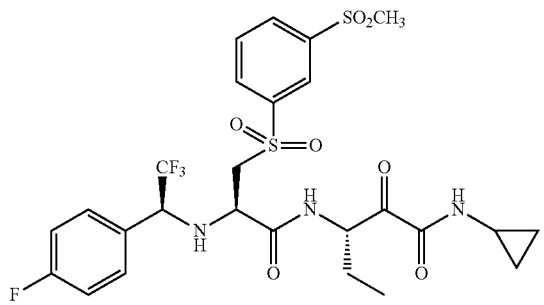 [SMILES: CC[C@H](NC(=O)[C@H](CS(=O)(=O)c1cccc(S(C)(=O)=O)c1)N[C@@H](c1ccc(F)cc1)C(F)(F)F)C(=O)C(=O)NC1CC1]

Step 1

To a stirred solution of (2R)-2-((2,2,2-trifluoro-1-(4-fluorophenyl)ethyl)amino)-3-(tritylthio)propanoic acid (30.0 g; 55.6 mmol), previously obtained as a 12:1 mixture of the (R,S)- and (R,R)-diastereomers, in methanol (80 mL) and toluene (60 mL) under nitrogen was cooled in an ice-water bath. A 2M solution of trimethyldiazomethane in hexane (55 mL; 110 mmol; 198 mole %) over a 1-h period. The reaction mixture was stirred in the ice bath for an additional 15 minutes then at ambient temperature for 1 hour after which time the reaction was determined to be complete by thin-layer chromatographic analysis (SiO$_2$; 4% methanol in dichloromethane). The reaction mixture was concentrated in vacuo to give a 37.3 g of a thick, dark brown oil. The residue was purified by chromatography (SiO$_2$; dichloromethane/hexane, 2:3 followed by, dichloromethane/hexane, 1:1) to give 24.85 g (80.8%) of (2R)-methyl 2-((2,2,2-trifluoro-1-(4-fluorophenyl)ethyl)amino)-3-(tritylthio)propanoate. Methods for preparation of starting materials are disclosed in U.S. Pat. No. 7, 696,250, which is incorporated herein in its entirety by reference with respect to such methods.

Step 2

To a stirred solution of (2R)-methyl 2-((2,2,2-trifluoro-1-(4-fluorophenyl)ethyl)amino)-3-(tritylthio)propanoate (24.8 g; 44.8 mmol) in anhydrous dichloromethane (200 mL), previously cooled to in an ice-water bath under nitrogen, was added trifluoroacetic acid (14 mL; 20.7 g; 182 mmol; 405 mole %), followed by triethylsilane (14.4 mL; 10.5 g; 90.1 mmol; 200 mole %). The reaction mixture was stirred at ambient temperature for 2 h then concentrated in vacuo. The residue was redistilled from dichloromethane and the residue absorbed onto silica gel (30 g). The absorbed sample was applied to a column of SiO$_2$ (660 g) and eluted with 2% ethyl acetate in hexane, gradually increased to 10% EtOAc in hexane to give 11.74 g (84.5%) of (2R)-methyl 3-mercapto-2-((2,2,2-trifluoro-1-(4-fluorophenyl)ethyl)amino)propanoate which was used directly in the next step. LC-MS, negative ion mode: m/z=310 [M−H]$^-$ (100%).

Step 3

A mixture of the (2R)-methyl 3-mercapto-2-((2,2,2-trifluoro-1-(4-fluorophenyl)ethyl)amino)propanoate (11.7 g; 37.5 mmol), (3-(methylsulfonyl)phenyl)boronic acid (15 g; 75 mmol; 200 mole %), anhydrous copper(II) acetate (10.22 g; 56.25 mmol; 150 mole %), activated powdered molecular sieves (11.5 g) and N,N-dimethylformamide (300 mL) was stirred under nitrogen. Pyridine (9.1 mL; 8.9 g; 113 mmol; 301 mole %) under nitrogen and the mixture was stirred at ambient temperature for 2 minutes. The green reaction mixture was heated to 110° C. for 2 hours then the reaction mixture was cooled to ambient temperature and filtered through celite. The filtrate was diluted with ethyl acetate and the mixture washed with 1N aqueous hydrochloric acid, followed by water, saturated aqueous sodium bicarbonate, water and finally saturated aqueous sodium chloride. The organic phase was dried (MgSO$_4$) and concentrated in vacuo to give ca 20.4 g of a brown oil, which was then suspended in hexane and triturated with sonication. Decantation of the liquid from the residue followed by distillation gave 18.8 g of a brown oil which was purified by chromatography (300 g of SiO$_2$; eluting with 5% ethyl acetate in hexane, followed by 10% ethyl acetate in hexane and finally 50% ethyl acetate in hexane. Evaporation of the appropriate fractions gave 12.7 g (56.6% based on a weight percent purity of 78%) of (2R)-Methyl 3-((3-(methylsulfonyl)phenyl)thio)-2-((2,2,2-trifluoro-1-(4-fluorophenyl)ethyl)amino)-propanoate which contained about 2.8 g of phenylmethylsulfone based on NMR integration.

Step 4

A solution of (2R)-methyl 3-((3-(methylsulfonyl)phenyl)thio)-2-((2,2,2-trifluoro-1-(4-fluorophenyl)-ethyl)amino)propanoate (12.7 g; 21 mmol based on a weight percent purity of 78%) in tetrahydrofuran (THF; 100 mL) was treated with a solution of lithium hydroxide monohydrate (2.8 g; 66 mmol; 314 mole %) in water (66 mL). The resulting mixture was stirred at ambient temperature for 30 minutes. The reaction mixture was cooled in an ice-water bath, acidified with 1N aqueous HCl (~80 mL) to pH 2. The mixture was diluted with ethyl acetate and the layers were separated. The aqueous phase was extrafted with ethyl acetate and the combined organic layers were washed with water, saturated aqueous sodium chloride and concentrated in vacuo to give 12.4 g of an oil, which contained about 2.8 g of phenylmethylsulfone by proton NMR.

The oil was dissolved in MTBE (150 mL) and a solution of dicyclohexylamine (4.5 mL; 4.1 g; 23 mmol; 105 mole %) in MTBE (50 mL) was added. The precipitated solid was filtered, washed with MTBE and hexane to give 12.05 g of the DCHA salt. The solid was recrystallized from hot acetonitrile (460 mL) to give 10.8 g of the purified salt. This material was recrystallized twice more from hot acetonitrile (38-39 mL/g) to give 10.0 g of the purified DCHA salt. This solid was suspended in MTBE and a 10% potassium hydrogensulfate solution was added. The organic phase was washed with water, saturated aqueous sodium chloride and dried (MgSO$_4$) to give 8.1 g (48% over 2 steps) of (R)-3-((3-(methylsulfonyl)phenyl)thio)-2-(((S)-2,2,2-trifluoro-1-(4-fluorophenyl)ethyl)amino)propanoic acid.

Step 5

Hydrogen peroxide (30%; 5.4 mL; 53.1 mmol; 300 mole %) was added dropwise to solution of (R)-3-((3-(methylsulfonyl)phenyl)thio)-2-(((S)-2,2,2-trifluoro-1-(4-fluorophenyl)ethyl)amino)propanoic acid (8.0 g; 17.7 mmol); sodium tungstate dihydrate (117 mg; 0.354 mmol; 2 mole %), tetra-n-butylammonium hydrogensulfate (240 mg; 0.708 mmol; 4 mole %) and phenylphosphonic acid (56 mg; 0.354 mmol; 2 mole %) in a mixture of toluene (50 mL) and ethyl acetate (5 mL). After the addition was complete, the reaction mixture was stirred for 2 h at ambient temperature. The reaction mixture was diluted with a solution of 15% aqueous sodium thiosulfate (300 mL). Ethyl acetate (300 mL) was then added and the biphasic mixture was cooled in an ice-water bath. The mixture was acidified to pH 1-2 using 4M aqueous hydrochloric acid. The layers were separated and the organic phase was washed with water followed by saturated aqueous sodium chloride. The resulting organic phase was dried ($MgSO_4$) and concentrated in vacuo until only a small volume. A small amount of a yellow solid was filtered and washed with ethyl acetate. The distillation was repeated and the suspension was diluted with MTBE then filtered. The filtrate was concentrated in vacuo to an oil to which hexane was added and the resulting mixture was sonicated. The mixture was cooled in an ice bath to initiate crystallization then the mixture was stored at −20° C. (freezer) overnight. The solid was filtered, washed with hexane and dried in a vacuum oven to give 8.36 g (97.1%) of (R)-3-((3-(methylsulfonyl)phenyl)sulfonyl)-2-(((S)-2,2,2-trifluoro-1-(4-fluorophenyl)ethyl)amino)-propanoic acid.

Step 6

A solution of (R)-3-((3-(methylsulfonyl)phenyl)sulfonyl)-2-(((S)-2,2,2-trifluoro-1-(4-fluorophenyl)ethyl)-amino)propanoic acid (7.3 g; 15 mmol) and HATU (6.84 g; 18.0 mmol; 120 mole %) in anhydrous dichloromethane (200 mL) was stirred at ambient temperature for 5 minutes, then (3S)-3-amino-N-cyclopropyl-2-hydroxypentanamide hydrochloride (35.0 mmol; 233 mole %) was added and the mixture stirred for 5 minutes. The reaction mixture was then cooled to 0-5° C. and treated with the dropwise addition of DIPEA (7.8 mL; 5.8 g; 45 mmol; 300 mol %). After the addition was complete, the cooling bath was removed and the reaction was stirred for 2.5 h at ambient temperature. The reaction mixture was concentrated in vacuo and partitioned between ethyl acetate and water. The layers were separated and the organic phase was washed in sequence with a solution of 10% aqueous potassium hydrogensulfate, water, 10% aqueous sodium bicarbonate, water, and finally saturated aqueous sodium chloride. The organic phase was dried ($MgSO_4$), and concentrated almost to dryness. The residue was triturated with diethyl ether then some hexane was added. The resulting solid was filtered and washed with hexane to give 8.6 g (96%) of (3S)—N-cyclopropyl-2-hydroxy-3-((R)-3-((3-(methylsulfonyl)phenyl)sulfonyl)-2-(((S)-2,2,2-trifluoro-1-(4-fluorophenyl)ethyl)amino)propanamido)pentanamide as an off-white solid. LC-MS, positive ion mode: m/z=638 [M+H]$^+$ (100%); negative ion mode: m/z=636 [M−H]$^-$ (100%). Methods for the preparation of starting materials are disclosed in U.S. Pat. No. 7,488,848.

Step 7

To a stirred solution of 9.6 g (15 mmol) of (3S)—N-cyclopropyl-2-hydroxy-3-((R)-3-((3-(methylsulfonyl)phenyl)sulfonyl)-2-(((S)-2,2,2-trifluoro-1-(4-fluorophenyl)ethyl)amino)propanamido)-pentanamide in a mixture of dichloromethane (200 mL) and acetonitrile (200 mL) was added under nitrogen was added DMP (8.9 g; 21 mmol; 140 mole %). The reaction mixture was stirred for 4 h at ambient temperature. The reaction mixture distilled in vacuo to remove about 150 mL of solvent and the resulting solution was diluted with ethyl acetate (1 L) then 1M sodium thiosulfate (250 mL) and saturated aqueous sodium bicarbonate (250 mL) were added. The biphasic mixture was stirred for 1 h and the layers were separated. The organic phase was concentrated to dryness and the residue co-distilled from dichloromethane.

The crude product was redissolved in dichloromethane (150 mL) and acetonitrile (50 mL) and DMP (1.3 g; 3.10 mmol; 21 mol %) was added in two portions. The reaction mixture was stirred for 2 h at ambient temperature then the reaction mixture was concentrated in vacuo. The residue was dissolved in ethyl acetate and stirred with 1M aqueous sodium thiosulfate and saturated aqueous sodium bicarbonate (250 mL). The layers were separated and the organic phase was washed with water, and saturated aqueous sodium chloride solution. The organic phase was dried ($MgSO_4$) and concentrated in vacuo to give 9.7 g of crude (S)—N-cyclopropyl-3-((R)-3-((3-(methylsulfonyl)phenyl)sulfonyl)-2-(((S)-2,2,2-trifluoro-1-(4-fluorophenyl)ethyl)amino)propanamido)-2-oxopentanamide as a foam. This material was dissolved in hot IPA (220 mL), which crystallized upon cooling. After allowing to cool overnight, the solid was filtered and washed on the filter with cold IPA (2×) followed by hexane. The solid was then dried in a vacuum oven at 40° C. to give 7.45 g (78%) of (S)—N-cyclopropyl-3-((R)-3-((3-(methylsulfonyl)phenyl)sulfonyl)-2-(((S)-2,2,2-trifluoro-1-(4-fluorophenyl)ethyl)amino)propanamido)-2-oxopentanamide (Compound B). LC-MS, positive ion mode: m/z=636 [M+H]$^+$ (100%); negative ion mode: m/z=634 [M−H]$^-$ (100%). $^{19}$F-NMR ($CDCl_3$) δ, ppm: −74.32 (s); −111.73 (s).

BIOLOGICAL EXAMPLES

Example 1

Cathepsin B Assay

Solutions of test compounds in varying concentrations were prepared in 101 μL of dimethyl sulfoxide (DMSO) and then diluted into assay buffer (40 μL, comprising: N,N-bis(2-hydroxyethyl)-2-aminoethanesulfonic acid (BES), 50 mM (pH 6); polyoxyethylenesorbitan monolaurate, 0.05%; and dithiothreitol (DTT), 2.5 mM). Human cathepsin B (0.025 pMoles in 25 μL of assay buffer) was added to the dilutions. The assay solutions were mixed for 5-10 seconds on a shaker plate, covered and incubated for 30 min at room temperature. Z-FR-AMC (20 nMoles in 25 μL of assay buffer) was added to the assay solutions and hydrolysis was followed spectrophotometrically at (λ 460 nm) for 5 min. Apparent inhibition constants ($K_i$) were calculated from the enzyme progress curves using standard mathematical models.

A number of compounds for use according to the invention were tested by the above-described assay and observed to exhibit cathepsin B inhibitory activity.

Example 2

Cathepsin K Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin K (0.0906 pMoles in 25 μL of assay buffer) was added to the dilutions. The assay solutions were mixed for 5-10 seconds on a shaker plate, covered and incubated for 30 min at room temperature. Z-Phe-Arg-AMC (4 nMoles in 25 μL of assay buffer) was added to the assay solutions and hydrolysis was followed spectrophotometrically at (λ 460 nm) for 5 min. Apparent inhibition constants ($K_i$) were calculated from the enzyme progress curves using standard mathematical models.

A number of compounds for use according to the invention were tested by the above-described assay and observed to exhibit cathepsin K inhibitory activity.

Example 3

Cathepsin L Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM). Human cathepsin L (0.05 pMoles in 25 μL of assay buffer) was added to the dilutions. The assay solutions were mixed for 5-10 seconds on a shaker plate, covered and incubated for 30 min at room temperature. Z-Phe-Arg-AMC (1 nMoles in 25 μL of assay buffer) was added to the assay solutions and hydrolysis was followed spectrophotometrically at ($\lambda$ 460 nm) for 5 min. Apparent inhibition constants ($K_i$) were calculated from the enzyme progress curves using standard mathematical models.

A number of compounds for use according to the invention were tested by the above-described assay and observed to exhibit cathepsin L inhibitory activity.

Example 4

Cathepsin S Assay

Solutions of test compounds in varying concentrations were prepared in 10 μL of dimethyl sulfoxide (DMSO) and then diluted into assay buffer (40 μL, comprising: MES, 50 mM (pH 6.5); EDTA, 2.5 mM; and NaCl, 100 mM); β-mercaptoethanol, 2.5 mM; and BSA, 0.00%. Human cathepsin S (0.05 pMoles in 25 μL of assay buffer) was added to the dilutions. The assay solutions were mixed for 5-10 seconds on a shaker plate, covered and incubated for 30 min at room temperature. Z-Val-Val-Arg-AMC (4 nMoles in 25 μL of assay buffer containing 10% DMSO) was added to the assay solutions and hydrolysis was followed spectrophotometrically (at $\lambda$ 460 nm) for 5 min. Apparent inhibition constants ($K_i$) were calculated from the enzyme progress curves using standard mathematical models.

A number of compounds for use according to the invention were tested by the above-described assay and observed to exhibit cathepsin S inhibitory activity of < or =100 nm.

Example 5

Cathepsin F Assay

Solutions of test compounds in varying concentrations were prepared in 10 μL of dimethyl sulfoxide (DMSO) and then diluted into assay buffer (40 μL, comprising: MES, 50 mM (pH 6.5); EDTA, 2.5 mM; and NaCl, 100 mM); DTT, 2.5 mM; and BSA, 0.01%. Human cathepsin F (0.1 pMoles in 25 μL of assay buffer) was added to the dilutions. The assay solutions were mixed for 5-10 seconds on a shaker plate, covered and incubated for 30 min at room temperature. Z-Phe-Arg-AMC (2 nMoles in 25 μL of assay buffer containing 10% DMSO) was added to the assay solutions and hydrolysis was followed spectrophotometrically (at $\lambda$ 460 nm) for 5 min. Apparent inhibition constants ($K_i$) were calculated from the enzyme progress curves using standard mathematical models.

A number of compounds for use according to the invention were tested by the above-described assay and observed to exhibit cathepsin F inhibitory activity.

Example 6

Cathepsin V Assay

The assays were performed similarly to those described above. Human Cathepsin V: The buffer used to assay this enzyme consisted of: 50 mM MES (pH 6.5), 2.5 mM DTT, 2.5 mM EDTA, 100 mM NaCl, 0.01% BSA and 10% DMSO. Recombinant human cathepsin V was supplied at 2.0 nM. Substrate, Z-Phe-Arg-AMC, was supplied at 25 μM. Apparent inhibition constants ($K_i$) were calculated from the enzyme progress curves using standard mathematical models.

A number of compounds for use according to the invention were tested by the above-described assay and observed to exhibit cathepsin V inhibitory activity of < or =100 nm.

PHARMACEUTICAL FORMULATION EXAMPLES

Example 1

Representative pharmaceutical formulations Containing a Compound of Formula (I)

Oral Formulation

| | |
|---|---|
| Compound of Formula (I) | 10-100 mg |
| Citric Acid Monohydrate | 105 mg |
| Sodium Hydroxide | 18 mg |
| Flavoring | |
| Water | q.s. to 100 mL |

Intravenous Formulation

| | |
|---|---|
| Compound of Formula (I) | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

Tablet Formulation

| | |
|---|---|
| Compound of Formula (I) | 1% |
| Microcrystalline Cellulose | 73% |
| Stearic Acid | 25% |
| Colloidal Silica | 1% |

Compound Bioassay Data

A. Cathepsin Inhibitory Profile of Compound A and Other Compounds for Use According to the Invention Compound A has a very high potency and selectivity when tested on multiple cathepsin enzymes (see, FIG. 1). The compound showed high potency in cells measured by inhibition of cathepsin S-dependent invariant chain processing $IC_{50}$<10 nM in Raji B cells. This compound also showed a high potency across species tested on the cathepsin S enzyme: monkey $IC_{50}$=<250 pM, mouse $IC_{50}$=<250 pM, rat $IC_{50}$=770 pM, dog $IC_{50}$=250 pM.

FIG. 2a illustrates the inhibition of cathepsin B and L activity by Compound A in endothelial cells. A single digit potency was observed. In addition, the compound is active in vivo as judged by accumulation of a biomarker in the spleen (see, FIG. 2b).

Compound C and Compound B also are potent inhibitors of cathepsins S, L, B and K as judged by their $IC_{50}$ values (see, FIG. 5).

B. Compound A Anti-Metastasis Activity

In in vitro bioassays for tumor invasiveness and angiogenesis, Compound A inhibited both tumor invasion and angiogenesis. Inhibition of cathepsin B and L activity by Compound A was observed in the endothelial cells (data not shown). A single digit nanomolar potency was observed. In addition, Compound A was active in vivo as judged by accumulation of a biomarker in the spleen of dosed animals (see, FIG. 2).

C. Compound A Treatment of Bone Cancer.

Figure 3B:
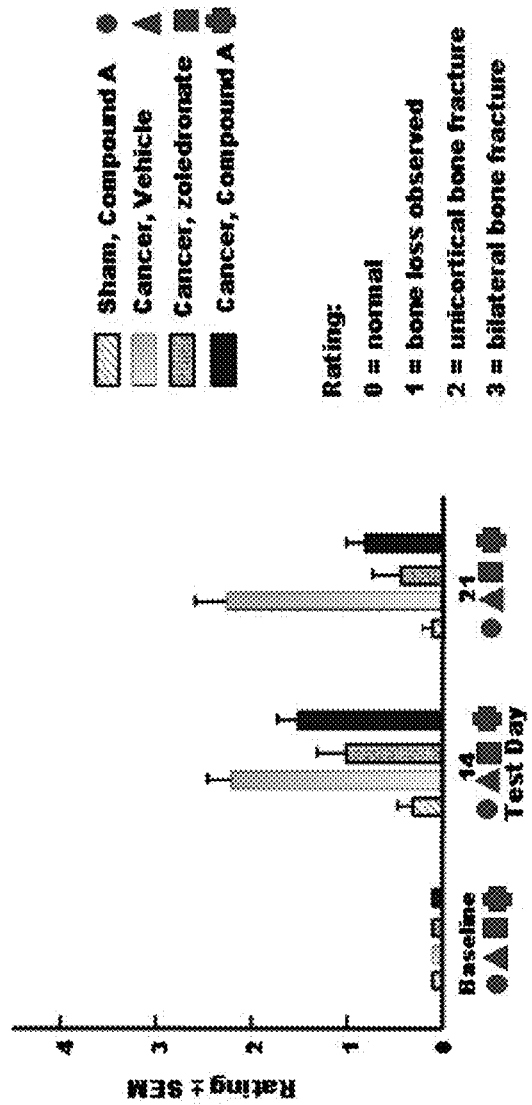
FIGS. 3b-3d. Left to right: Sham/media +Compound A, Cancer +vehicle, cancer +zoledronate, cancer +Compound A.
Figure 3C:
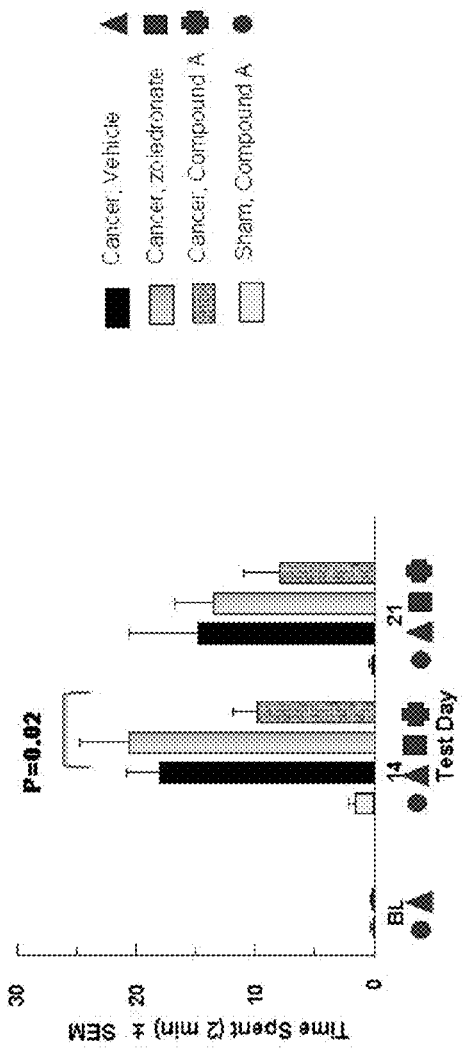
Figure 3D:
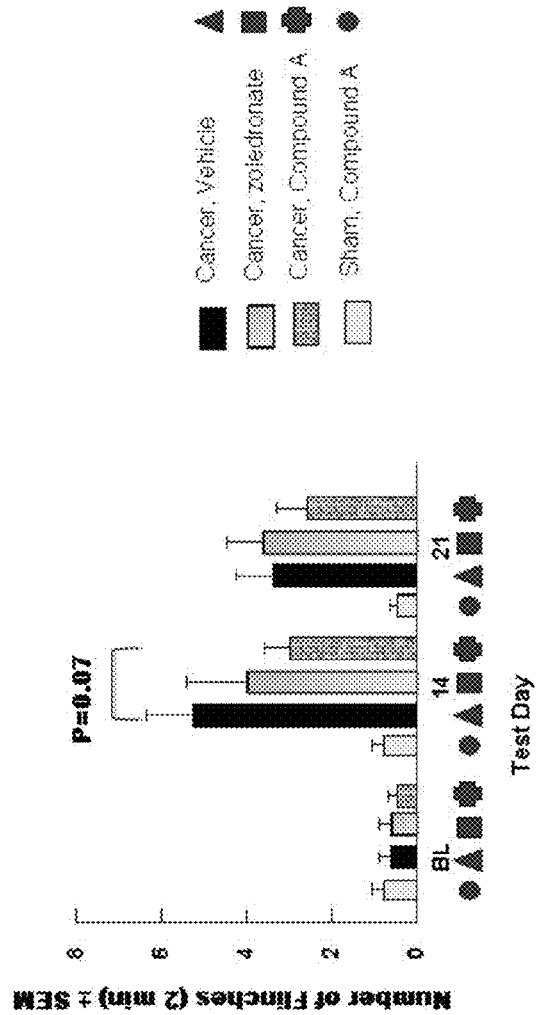
Figure 3E:
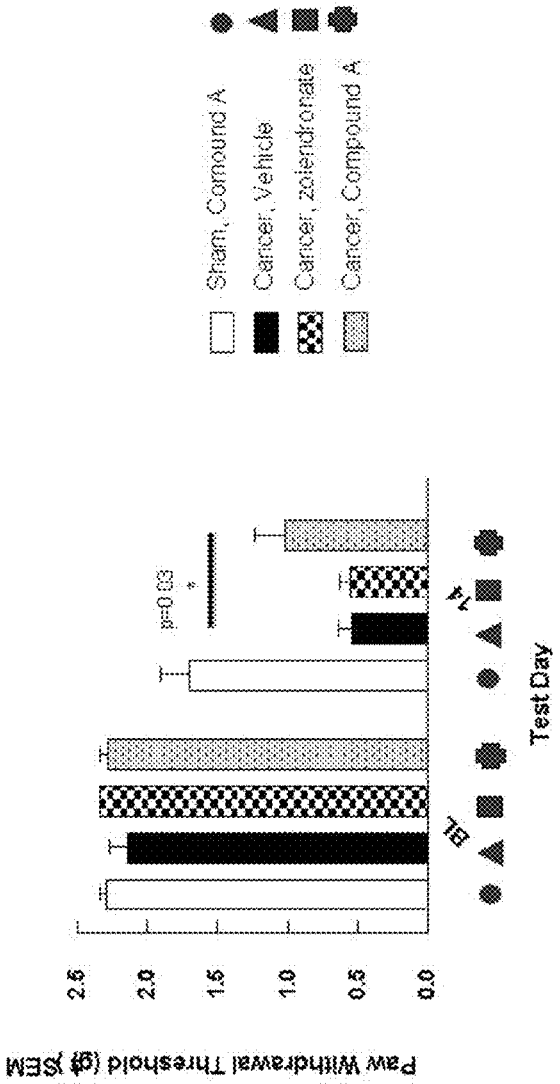
FIG. 3e shows the effects on movement evoked pain. Movement evoked pain was attenuated by Compound A on day 13 with statistical significance as compared to vehicle.

FIG. 3a sets forth the treatment protocol for the bone cancer pain study with Compound A. Dose groups: Vehicle, Zoledronate (100 µg/kg) positive control, Compound A (100 mg/kg, daily dosing, SC, days 7-21), 10 animals per group. Mice were implanted with breast cancer cells in the femur on day 0 and treated with Compound A on days 7 through 21. On days 0, 7, 14, and 21 radiographic imaging, thermal hyperalgesia, tactile allodynia, movement-evoked and spontaneous pain measurements were taken. Pain measurements were made 6 hours after dosing. Control animals were injected with media (and no tumor cells) in the femur. At day 21 animals with bone cancer begin weight loss; animals receiving Compound A retained weight as compared to vehicle and this may translate to increased survival time (data not shown). Bone destruction was attenuated by Compound A on day 14 and day 21 as compared to vehicle. The efficacy was similar to that obtained with zoledronate (see, FIG. 3b). Spontaneous pain in the form of Guarding was attenuated by Compound A on day 14 and day 21 with statistical significance as compared to vehicle or zoledronate, suggesting a direct analgesic effect; this readout is the key pain endpoint in this model and more directly applicable to the spontaneous pain seen in human bone cancer (see, FIG. 3c). Spontaneous Pain in the form of Flinching was attenuated by Compound A on day 14 and day 21 with statistical significance, as compared to vehicle (see, FIG. 3d). Compound A was without any significant effect after 7 days of drug washout. Movement evoked pain was attenuated by Compound A on day 13 with statistical significance as compared to vehicle (see, FIG. 3e).

D. Pharmacokinetic Profile of Compound A

Figure 4:
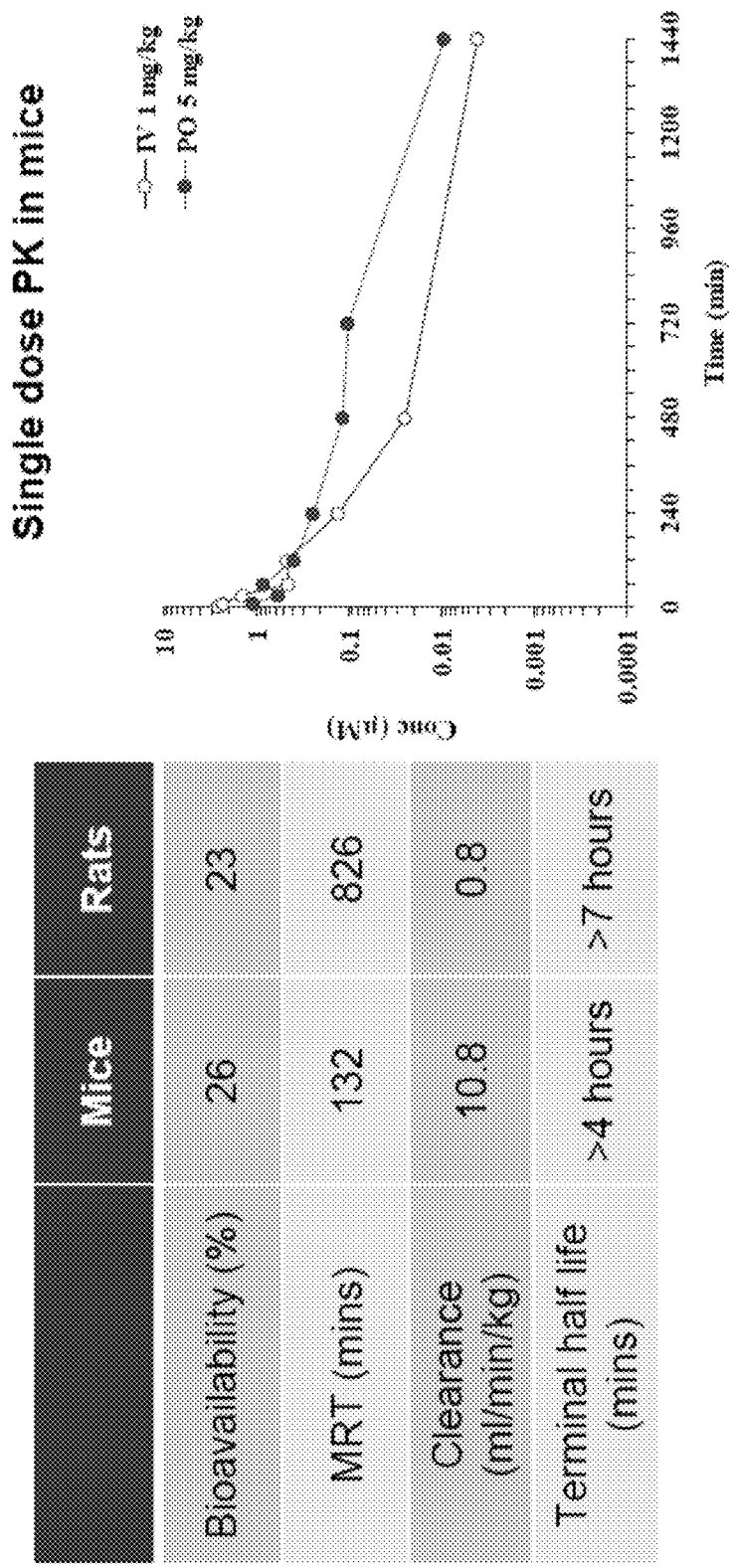
FIG. 4. Pharmacokinetics of Compound A.

As judged by its pharmacokinetic parameters for both rats and mice, Compound A has very favorable pharmacokinetics in test animals which indicate once daily dosing would be therapeutically feasible (see, FIG. 4).

E. Histology Analysis of Bone Samples in Bone Cancer Pain Study

Figure 6:
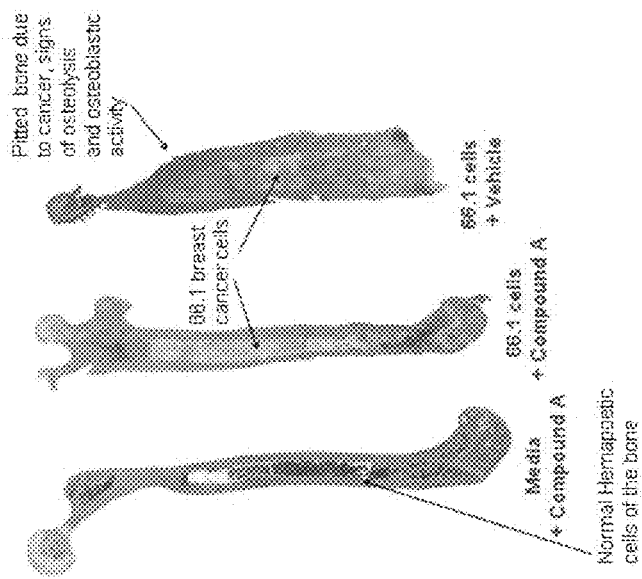
FIG. 6. Histology Analysis of Bone Samples in Bone Caner Pain Study. Representative bone sections from the study described in FIG. 3A were subjected to staining with the standard hematoxylin and eosin histological stain to visualize cellular structures in the bone.

FIG. 6 shows bone histology in the bone cancer pain pharmacology model, which was assessed with hemotoxylin and eosin staining which indicates tumor cell growth in the bone. FIG. 6 also shows that the associated bone pitting is reduced by compound A dosing. Compound A was dosed subcutaneously, at a 100 mg/kg dose once a day, in a nanoparticle-sized formulation suitable for subcutaneous dosing and diluted in D5W (sterile 5% dextrose in water). Dosing was initiated 7 days after the femur implantation of the 66.1 tumor cells and continued once a day.

The data in FIG. 6 is based on representative bone sections from the study described in FIG. 3A, which were subjected to staining with the standard histological stain hematoxylin and eosin, in order to visualize cellular structures in the bone. Visualized samples include bone sections from study animals with 66.1 tumor cells injected into bone and dosed with either vehicle control or compound A and also animals with media alone injected into bone and also dosed with compound A. Normal hemapoetic cells of the bone and the 66.1 cancer cells within the bone, as well as bone histomorphology, were visualized by this staining procedure. FIG. 6 shows that pitting of the bone is indicated from samples in the study arm with 66.1 cancer cells in the bone and dosed with vehicle control only. This is due to ostelytic activity induced by the presence of the 66.1 cancer cells in the bone.

F. Inhibition of Bone Resorption In Vitro

These results showed that Compound A inhibits bone resorption in vitro in an assay using differentiated human primary osteoclasts and bovine bone. These results showed that Compound A demonstrated an $EC_{50}$=312 nM (See FIG. 6). Compound A was assessed in an in vitro assay for its efficacy in blocking resorption activity of human osteoclasts in vitro. Bone marrow-derived human osteoclast precursor cells were cultured on bovine bone slices for 7 days in conditions that allowed osteoclast differentiation, and allowing them to differentiate into bone-resorbing osteoclasts. After completion of osteoclast differentiation at day 7, the culture medium was removed and new culture medium for assessing osteoclast activity was added. Test compounds including Compound A was added to the cultures at this stage on day 7. Cultures were then allowed to continue for an additional 3 days allowing them to resorb bone. Concentrations of Compound assessed were 1, 3, 10, 30, 100, 300, and 1000 nM in 8 replicates. Tartrate-resistant acid phosphatase 5b activity (TRACP 5b) was measured from the culture medium collected on day 7 indicating the number of mature osteoclasts formed in each well before adding compounds. C-terminal cross-linked telopeptides of type 1 collagen (CTX) were measured form the culture medium collected at day 10 to quantitate bone resorption during days 7-10. A resorption index demonstrating mean osteoclast activity was calculated by dividing the obtained CTX values at day 10 with obtained TRACP 5b values at day 7. The study was performed in 95 well plates with each containing a baseline group including vehicle, a control group with a reference compound E64, and 7 concentrations of the test compound to determine an EC50 for inhibition of resorption activity.

G. Inhibition of Bone Resorption In Vitro

Figure 7:
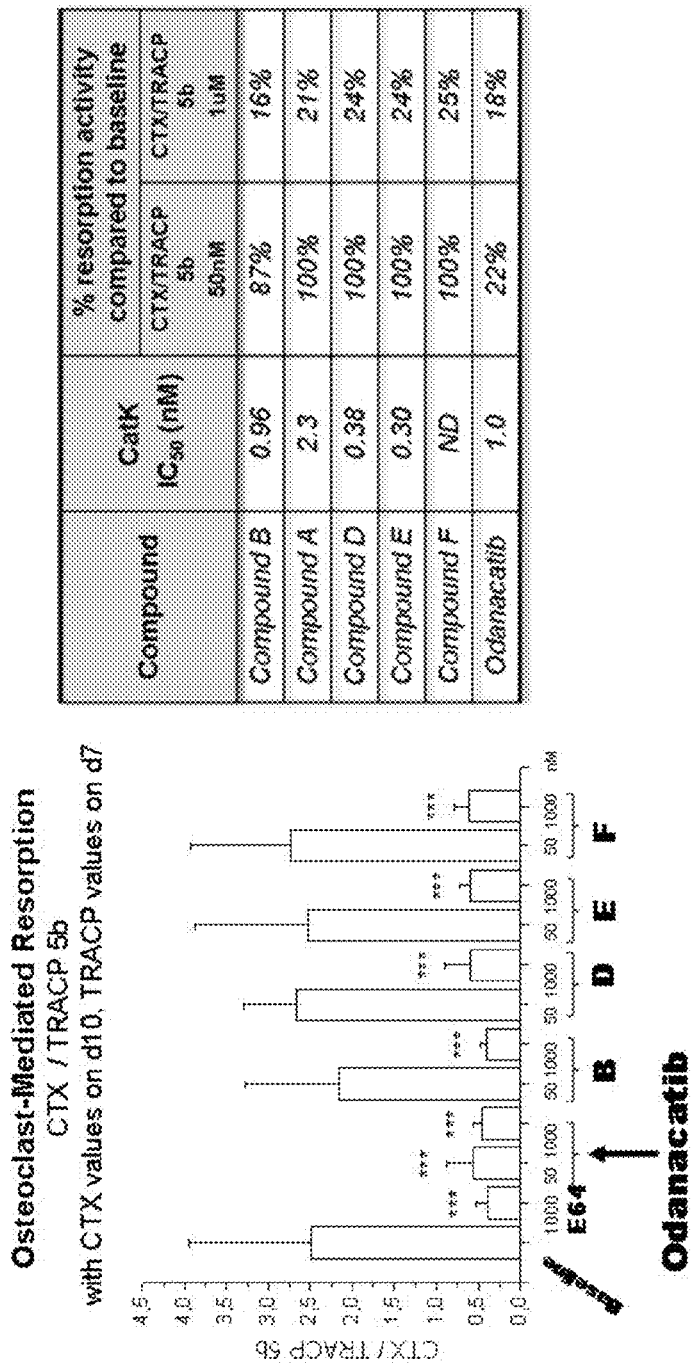
FIG. 7. Inhibition of Bone Resorption In Vitro.

These results showed that the additional compounds assessed, e.g., B, D, E, and F, also inhibit bone resorption in vitro, with similar potency to Compound A (see, FIG. 7). The bar graph in FIG. 7 shows actual values for CTX/TRACP5b. The Table in FIG. 7 shows the percentage of the level of activity relative to the level from the baseline without compound added, which was set forth as 100%. The experimental procedure for the assay for in vitro bone resorption is as described above and herein.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

What is claimed is:

1. A method of reducing metastatic cancer bone pain; said method comprising administration to a subject in need thereof a therapeutically effective amount of a cathepsin S/K inhibitor, a cathepsin S/K/B inhibitor, a cathepsin S/K/L inhibitor or a S/K/L/B inhibitor, wherein the inhibitor is a compound of Formula (I):

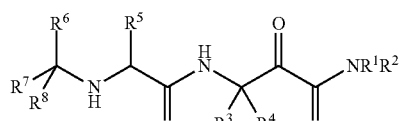

where:
R¹ is hydrogen or alkyl;
R² is cycloalkyl or cycloalkylalkyl optionally substituted with one or two substituents independently selected from alkyl, alkoxy or halo;
R³ is hydrogen or alkyl;
R⁴ is hydrogen, alakyl, or cycloalkyalkyl;
R⁵ is haloalkyl, (alkylene or haloalkylene)-X—R⁹ (where X is a bond, —O—, —S—, —SO—, —SO₂—, or —NHSO₂— and R⁹ is alkyl, haloalkyl, cycloalkyl, cycloalkylalkyl, pyrimidinyl, pyridinylalkyl, phenyl or phenylalkyl) wherein the alicyclic, pyridinyl, or phenyl ring in R⁵ is optionally substituted with one, two, or three Rᵃ independently selected from alkyl, haloalkyl, alkoxy, hydroxy, halo, or haloalkoxy or optionally substituted with one or two Rᵇ independently selected from hydrogen, alkyl, haloalkyl, alkoxy, hydroxy, haloalkoxy, halo, and one Rᶜ selected from or —SO₂R¹¹ (where R¹¹ is alkyl);
R⁶ is hydrogen or haloalkyl;
R⁷ is hydrogen, alkyl, or haloalkyl; and
R⁸ is phenyl or phenoxy-CF₂— wherein the phenyl or phenoxy is optionally substituted with one, two, or three Rᵉ independently selected from alkyl, halo, haloalkyl, hydroxy, alkoxy, and haloalkoxy; or a pharmaceutically acceptable salt thereof.

2. The method of claim 1, wherein the pain is inflammatory pain, neuropathic pain, nerve pain, or breakthrough pain.

3. The method of claim 2, wherein the pain is due to bone microfractures, bone distortion, mechanical stress, or disruption of the periosteum with stretching and entrapment of nerves.

4. A method for treating a metastatic breast cancer in bone, said method comprising administration to a subject in need thereof a therapeutically effective amount of a compound selected from the group consisting of

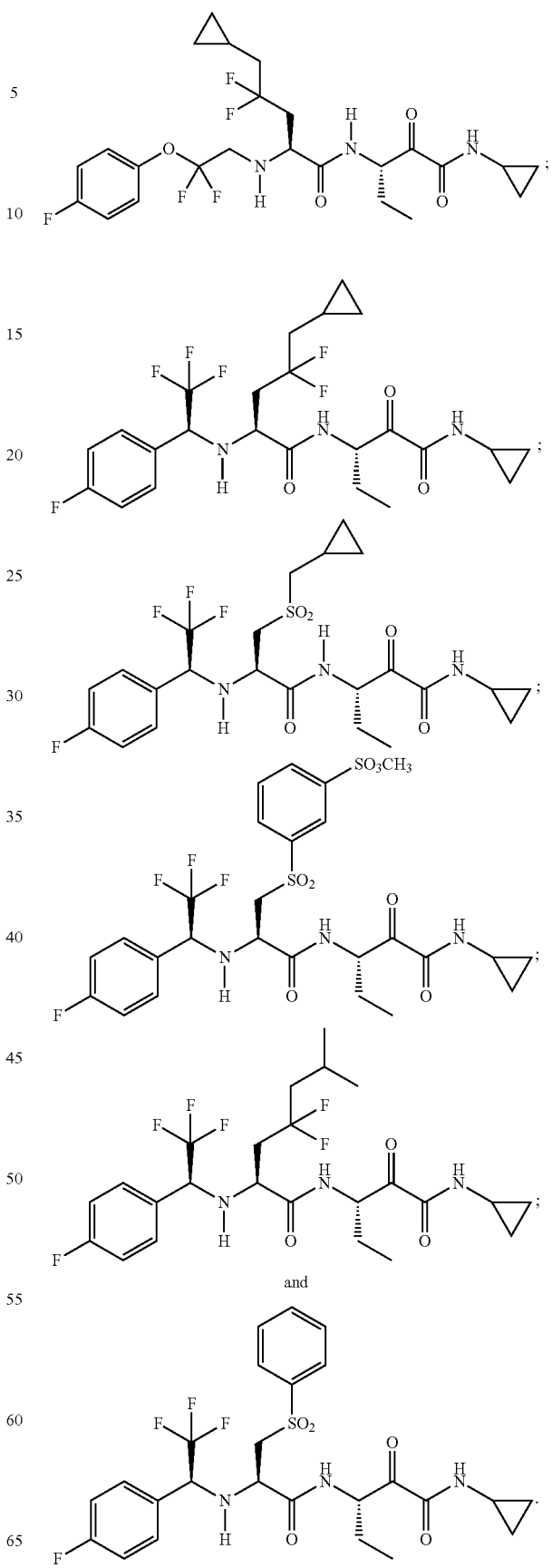

5. The method of claim 4, wherein the inhibitor is
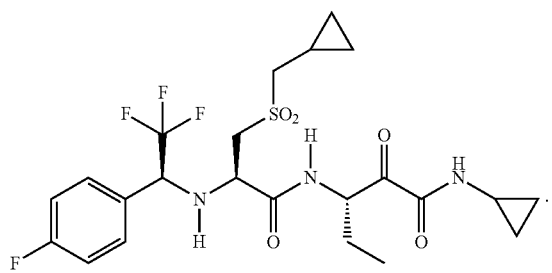
6. The method of claim 1, wherein the inhibitor is selected from the group consisting of
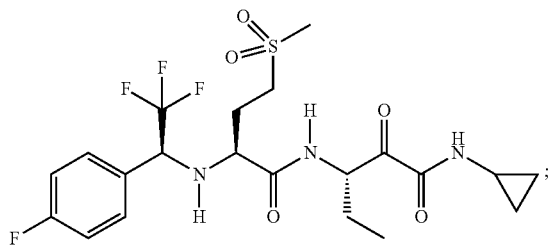
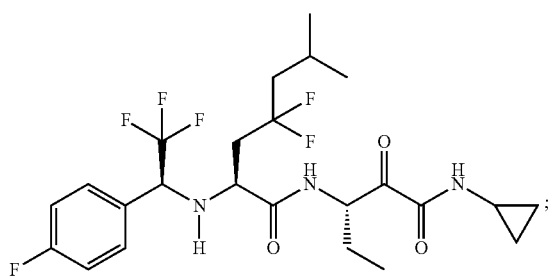
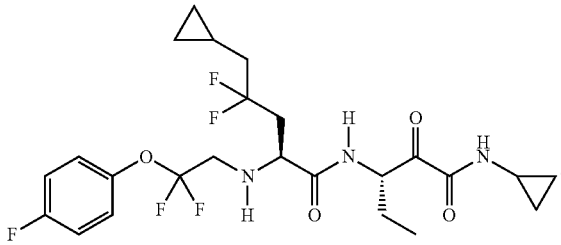
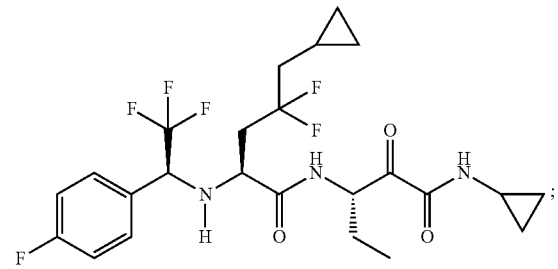 [SMILES: CC[C@H](NC(=O)[C@H](CS(=O)(=O)CC1CC1)N[C@@H](c1ccc(F)cc1)C(F)(F)F)C(=O)C(=O)NC1CC1]
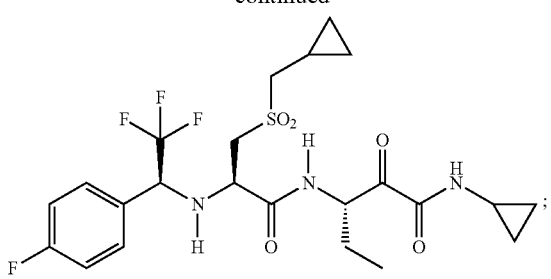
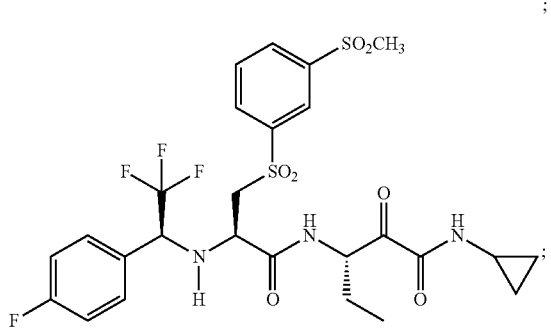
and
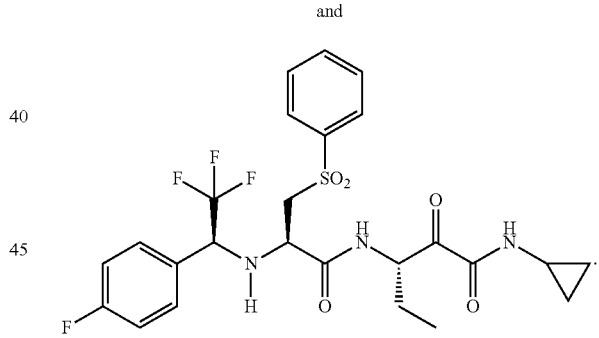
7. A method for treating a metastatic multiple myeloma in bone, said method comprising administration to a subject in need thereof a therapeutically effective amount of a compound selected from the group consisting of
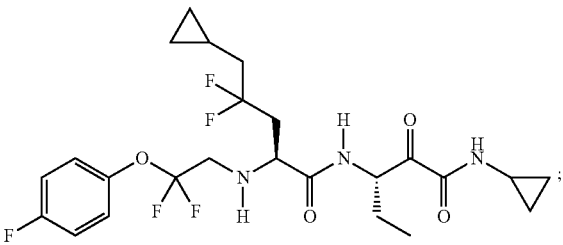

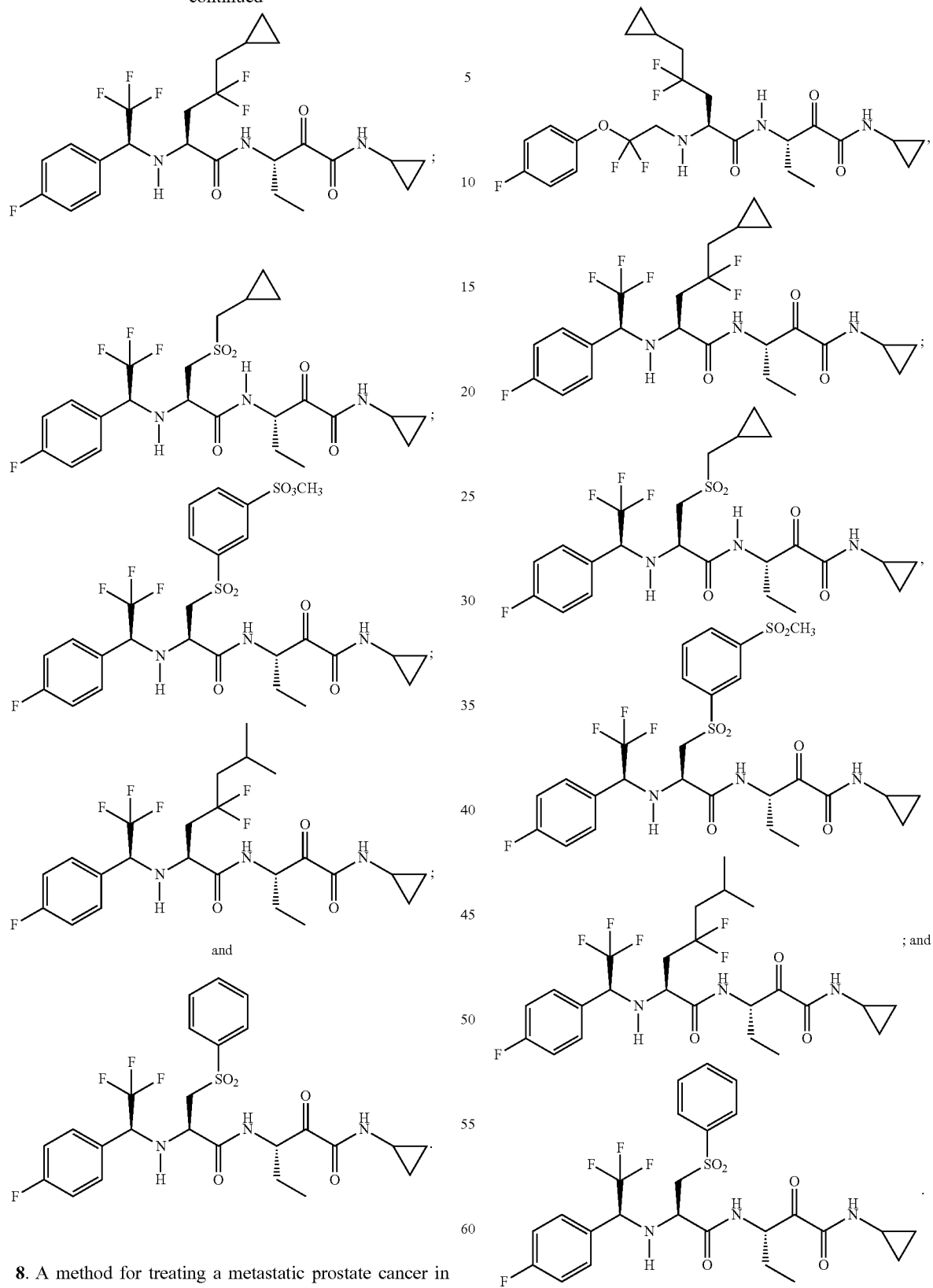
8. A method for treating a metastatic prostate cancer in bone, said method comprising administration to a subject in need thereof a therapeutically effective amount of a compound selected from the group consisting of
* * * * *